US007417159B2

(12) United States Patent
Galvez et al.

(10) Patent No.: US 7,417,159 B2
(45) Date of Patent: Aug. 26, 2008

(54) CONJUGATED LINOLENIC ACIDS AND METHODS OF PREPARATION AND PURIFICATION AND USES THEREOF

(75) Inventors: Juan-Miguel Garro Galvez, Sherbrooke (CA); Paul Angers, Sainte-Foy (CA); Sandie Briand, Sherbrooke (CA)

(73) Assignee: Universite Laval, Quebec (CA)

( * ) Notice: Subject to any disclaimer, the term of this patent is extended or adjusted under 35 U.S.C. 154(b) by 0 days.

(21) Appl. No.: 10/567,419

(22) PCT Filed: Aug. 6, 2004

(86) PCT No.: PCT/CA2004/001470

§ 371 (c)(1),
(2), (4) Date: Aug. 21, 2006

(87) PCT Pub. No.: WO2005/014516

PCT Pub. Date: Feb. 17, 2005

(65) Prior Publication Data

US 2006/0281815 A1  Dec. 14, 2006

(30) Foreign Application Priority Data

Aug. 6, 2003  (CA)  .................................. 2436650

(51) Int. Cl.
*C07B 35/08* (2006.01)
(52) U.S. Cl. ........................... 554/126; 554/1; 554/224; 554/175; 514/784
(58) Field of Classification Search .............. 554/1, 554/126, 224, 175; 514/784
See application file for complete search history.

(56) References Cited

U.S. PATENT DOCUMENTS

| 2,242,230 A | 5/1941 | Burr et al. |
|---|---|---|
| 2,343,644 A | 3/1944 | Cawley |
| 2,350,583 A | 6/1944 | T. Bradley |
| 2,389,260 A | 11/1945 | Kirschenbauer |
| 2,487,890 A | 11/1949 | Harvey |
| 3,162,658 A | 12/1964 | Josef et al. |
| 3,984,444 A | 10/1976 | Ritz et al. |
| 4,058,594 A | 11/1977 | Williams |
| 4,164,505 A | 8/1979 | Krajca et al. |
| 4,381,264 A | 4/1983 | Struve |
| 4,393,049 A | 7/1983 | Horrobin |
| 4,499,010 A * | 2/1985 | Tanino et al. ............... 252/512 |
| 4,535,093 A | 8/1985 | Horrobin |
| 4,666,701 A | 5/1987 | Horrobin et al. |
| 4,681,896 A | 7/1987 | Horrobin |
| 4,721,584 A | 1/1988 | Arai et al. |
| 4,758,592 A | 7/1988 | Horrobin et al. |
| 4,776,984 A | 10/1988 | Trailer et al. |
| 4,806,569 A | 2/1989 | Horrobin |
| 4,826,877 A | 5/1989 | Stewart et al. |
| 4,851,431 A | 7/1989 | Yehuda |
| 4,855,136 A | 8/1989 | Horrobin et al. |
| 4,868,212 A | 9/1989 | Horrobin |
| 4,888,326 A | 12/1989 | Horrobin |
| 4,898,885 A | 2/1990 | Horrobin |
| 4,920,098 A | 4/1990 | Cotter et al. |
| 4,965,075 A | 10/1990 | Horrobin et al. |
| 4,970,235 A | 11/1990 | Traitler et al. |
| 4,997,657 A | 3/1991 | Horrobin et al. |
| 5,002,767 A | 3/1991 | Masse |
| 5,011,855 A | 4/1991 | Traitler et al. |
| 5,120,763 A | 6/1992 | Yehuda |
| 5,128,152 A | 7/1992 | Horrobin et al. |
| 5,147,854 A | 9/1992 | Newman |
| 5,196,198 A | 3/1993 | Shaw et al. |
| 5,223,285 A | 6/1993 | Demichele et al. |
| 5,288,755 A | 2/1994 | Yehuda |
| 5,312,834 A | 5/1994 | Yeo |
| 5,324,748 A | 6/1994 | Horrobin |
| 5,378,732 A | 1/1995 | Horrobin et al. |
| 5,380,757 A | 1/1995 | Horrobin |
| 5,416,114 A | 5/1995 | Yehuda |
| 5,428,072 A | 6/1995 | Cook et al. |
| 5,430,066 A | 7/1995 | Cook et al. |
| 5,468,776 A | 11/1995 | Yehuda |
| 5,494,924 A | 2/1996 | Cavazza et al. |
| 5,541,225 A | 7/1996 | Leaf et al. |
| 5,554,646 A | 9/1996 | Cook et al. |
| 5,576,666 A | 11/1996 | Rauvola |
| 5,580,556 A | 12/1996 | Horrobin |
| 5,585,400 A | 12/1996 | Cook et al. |
| 5,591,446 A | 1/1997 | Melnik et al. |
| 5,599,840 A | 2/1997 | Yehuda |
| 5,604,216 A | 2/1997 | Horrobin |
| 5,612,074 A | 3/1997 | Leach |

(Continued)

FOREIGN PATENT DOCUMENTS

CA  2393403  6/2001

(Continued)

OTHER PUBLICATIONS

Adlof, R.O. (1999) "Preparation of unlabeled and isotope-labeled conjugated linoleic and related fatty acid isomers," (In: Yurawecz et al. (Ed), *Advances in Conjugated Linoleic Acid Research*, vol. 1, AOCS Press, Champaign, IL, pp. 21-37.

(Continued)

*Primary Examiner*—Janet L. Andres
*Assistant Examiner*—Sudhakar Katakam
(74) *Attorney, Agent, or Firm*—Knobbe Martens Olson & Bear LLP

(57) ABSTRACT

This invention relates to a new conjugated linoleic acids, a process for preparation thereof and method of use. Thus this invention is concerned with the preparation and purification of conjugated linoleic acids from materials rich in alpha or gamma linoleic acids. The reaction produces a mixture containing a 1:1 ratio of 9Z, 11E, 15Z-octadecatrienoic acid and 9Z, 13E, 15Z-octadecatrieonic acid. The mixture can be purified up to 90% by liquid chromatography, crystallization or urea crystallization. The mixture of 1:1 9Z, 11E, 15Z-octadecatrienoic acid and 9Z, 13E, 15E, 15Z-octadecatrienoic acid have anticancerous activities.

24 Claims, 12 Drawing Sheets

U.S. PATENT DOCUMENTS

| | | | |
|---|---|---|---|
| 5,626,849 A | 5/1997 | Hastings et al. |
| 5,661,180 A | 8/1997 | Demichele et al. |
| 5,668,174 A | 9/1997 | Kawagishi et al. |
| 5,670,540 A | 9/1997 | Horrobin et al. |
| 5,672,726 A | 9/1997 | Ryu et al. |
| 5,674,901 A | 10/1997 | Cook et al. |
| 5,679,809 A | 10/1997 | Bertoli et al. |
| 5,756,088 A | 5/1998 | Matsuura et al. |
| 5,763,484 A | 6/1998 | Horrobin |
| 5,798,348 A | 8/1998 | Alemany |
| 5,804,210 A | 9/1998 | Cook et al. |
| 5,814,663 A | 9/1998 | Cook et al. |
| 5,837,731 A | 11/1998 | Vaddaki |
| 5,840,715 A | 11/1998 | Florio |
| 5,859,055 A | 1/1999 | Horrobin et al. |
| 5,892,074 A | 4/1999 | Seidel |
| 5,898,074 A | 4/1999 | Prasad |
| 5,914,346 A | 6/1999 | Cook et al. |
| 5,928,478 A | 7/1999 | Berg |
| 5,962,712 A | 10/1999 | Demichele et al. |
| 5,986,116 A | 11/1999 | Iwata et al. |
| 5,998,476 A | 12/1999 | Sleigh et al. |
| 6,020,378 A | 2/2000 | Cook et al. |
| 6,034,132 A | 3/2000 | Remmereit |
| 6,063,820 A | 5/2000 | Cavazza |
| 6,077,828 A | 6/2000 | Abbruzzese |
| 6,136,795 A | 10/2000 | Florio |
| 6,160,140 A | 12/2000 | Bhaggan et al. |
| 6,160,141 A | 12/2000 | Seidel |
| 6,177,470 B1 | 1/2001 | Horrobin et al. |
| 6,177,580 B1 | 1/2001 | Timmermann et al. |
| 6,245,811 B1 | 6/2001 | Horrobin et al. |
| 6,258,846 B1 | 7/2001 | Hermelin et al. |
| 6,271,404 B1 | 8/2001 | Bhaggan et al. |
| 6,316,645 B1 * | 11/2001 | Sih et al. | 554/126 |
| 6,319,950 B1 | 11/2001 | Seidel et al. |
| 6,326,355 B1 | 12/2001 | Abbruzzese |
| 6,340,705 B1 | 1/2002 | Obukowicz et al. |
| 6,342,619 B2 | 1/2002 | Seidel |
| 6,380,253 B1 | 4/2002 | Das |
| 6,387,883 B1 | 5/2002 | Abbruzzese |
| 6,409,649 B1 | 6/2002 | Reaney |
| 6,414,171 B1 | 7/2002 | Reaney |
| 6,420,577 B1 | 7/2002 | Reaney et al. |
| 6,426,367 B1 | 7/2002 | Das et al. |
| 6,459,599 B1 | 10/2002 | Agirman et al. |
| 6,479,683 B1 | 11/2002 | Abney et al. |
| 6,502,908 B1 | 1/2003 | Mueller et al. |
| 6,596,302 B2 | 7/2003 | O'connor et al. |
| 6,602,908 B2 | 8/2003 | Seidel |
| 6,617,354 B1 | 9/2003 | Das |
| 6,664,405 B2 * | 12/2003 | Lee | 554/186 |
| 2002/0077317 A1 | 6/2002 | Das et al. |
| 2002/0077362 A1 | 6/2002 | Lee et al. |
| 2003/0157147 A1 | 8/2003 | Hoge et al. |
| 2004/0116513 A1 | 6/2004 | Focant et al. |

FOREIGN PATENT DOCUMENTS

| | | |
|---|---|---|
| CA | 2471649 | 6/2003 |
| CA | 2396840 | 2/2004 |
| CN | 1356386 | 7/2002 |
| CN | 1200089 C | 5/2005 |
| EP | 037175 | 10/1981 |
| EP | 078434 | 5/1983 |
| EP | 086092 | 8/1983 |
| EP | 087863 | 9/1983 |
| EP | 087864 | 9/1983 |
| EP | 087865 | 9/1983 |
| EP | 106571 | 4/1984 |
| EP | 145873 | 6/1985 |
| EP | 211502 | 2/1987 |
| EP | 309086 | 3/1989 |
| EP | 416855 | 3/1991 |
| EP | 421867 | 4/1991 |
| EP | 516034 | 12/1992 |
| EP | 598365 | 5/1994 |
| EP | 696453 | 2/1996 |
| EP | 0 579 901 B1 | 3/1996 |
| EP | 891773 | 1/1999 |
| GB | 558881 | 1/1944 |
| JP | 2000336029 * | 5/2000 |
| JP | 2000/336029 | 12/2000 |
| JP | 02000336029 A * | 12/2000 |
| JP | 2003171272 | 6/2003 |
| WO | WO 87/07263 | 12/1987 |
| WO | WO 88/02221 | 4/1988 |
| WO | WO 94/05319 | 3/1994 |
| WO | WO 94/10125 | 5/1994 |
| WO | WO 95/13806 | 5/1995 |
| WO | WO 98/21949 | 5/1998 |
| WO | WO 99/32105 | 7/1999 |
| WO | WO 01 44485 | 6/2001 |
| WO | WO 2004/013078 | 2/2004 |

OTHER PUBLICATIONS

Aneja, R.P. et al. (1990) "Conjugated linoleic acid contents of indian curds and ghee," *Indian J. Dairy Sci*, 43: 231-238.

Berdeaux, O. et al. (1997) "Large-scale synthesis of methyl cis-9, trans-11-octadecadienoate from methyl ricinoleate," *JAOCS* 74:1011-1015.

Birt, D.F. et al. (1992) "Dietary energy and fat effects on tumor promotion," *Cancer Research*, (Suppl.) 52:2035s-2039s.

Chin, S.F. et al. (1992) "Dietary sources of conjugated dienoic isomers of linoleic acid, a newly recognized class of anticarcinogens," *J. Food Composition and Analysis* 5:185-197.

Gunstone, F.D. et al. (1971) "Fatty Acids, Part 29, methyl 12-mesyloxyoleate as a source of cyclopropane esters and of conjugated octadecadienoates," *Chem. Phys. Lipids* 7:121-134.

Ha, Y.L et al. (1990) "Inhibition of benzo(a)pyrene-induced mouse forestomach neoplasia by conjugated dienoic derivatives of linoleic acid," *Cancer Res*. 50:1097-1101.

Hopkins, C.Y. (1972) "Fatty acids with conjugated unsaturation," (In Gunstone, F.D. (Ed), *Topics in Lipid Chemistry*, vol. 3 ELEK Science, London, pp. 37-87.

Igarashi, M. et al. (2000) "Newly recognized cytotoxic effect of conjugated trienoic fatty acids on cultured human tumor cells," *Cancer Letters* 148:173-179.

IP, C. (1997) "Review of the effects of trans fatty acids, oleic acid, n-3 polyunsaturated fatty acids, and conjugated linoleic acid on mammary carcinogenesis in animals," *Am. J. Clin. Nutr*. 66 (suppl): 1523S-5929S.

Kass, J.P. et al. (1939) "A Note on the constitution of linoleyl alcohol prepared by the sodium reduction of linoleic acid," *J. Am. Chem. Soc.* 61:482-483.

Kass, J.P. et al. (1939) "Pseudo-eleostearic acid," *J. Amer. Chem. Soc.* vol. 61:3292-3294.

Kepler, C. R. et al. (1967) "Biohydrogenation of unsaturated fatty acids. III. Purification and properties of a linoleate $\in^{12}$-CIS, $\in^{11}$-trans-isomerase from *Butyrivibrio fibrisolvens*," *J. Biol. Chem.* 242:5686-5692.

Kepler, C.R. et al. (1966) "Intermediates and products of the biohydrogenation of linoleic acid by *Butyrivibrio fibrisolvens*," *J. Biol. Chem*. 241:1350-1354.

Lee, K.N. et al. (1994) "Conjugated linoleic acid and atherosclerosis in rabbits," *Atherosclerosis* 108:19-25.

Moore, T. (1937) "Spectroscopic changes in fatty acids: I. changes in the absorption spectra of various fats induced by treatment with potassium hydroxide," *J. Biochem*. 31: 138-154.

Pariza, M.W. et al. (2001) "The biological active isomers of conjugated linoleic acid," *Prog. Lipid Res*. 40:283-298.

Parodi, P.W. (1977) "Conjugated octadecadienoic acids of milk fat," *J. Dairy Sci*. 60:1550-1553.

Radlove, S.B. et al. (1946) "Catalytic isomerization of vegetable oils," *Ind. Eng. Chem* 38:997-1002.

Sagredos, A.N. (1974) "Formation of idanyl derivatives from trienoic acids," Fette, Seifen, anstrichmittel 76:8-16, Unilever forschungsges, m.b.H., Hamburg, Fed. Rep. Germany.

Shantha, N.C. et al. (1993) "Conjugated linoleic acid concentrations in processed cheese containing hydrogen donors, iron and dairy-based additives," *Food Chemistry* 47:257-261.

Shantha, N.C. et al. (1995) "Conjugated linoleic acid concentrations in dairy products as affected by processing and storage," *J. Food Science* 60:695-697.

Strocchi, A. (1969) "Comparison between the mechanisms of alkaline isomerization and autooxidation of polyunsaturated C18 fatty acids," Univ. Bolonga, Bologna, Italy Revue Francaise des corps Gras 16:3-13.

Takagi, T. et al. (1981) "Occurrence of mixtures of geometrical isomers of conjugated octadecatrienoic acids in some seed oils: analysis by open-tubular gas liquid chromatography and High Performance Liquid Chromatography," *Lipids* 16:546-551.

Yuraweca, M.P. et al. (1993) "Estimation of conjugated octadecatrienes in edible fats and oils," *JAOCS* 70:1093-1099.

* cited by examiner

1. Palmitic Acid
2. Stearic Acid
3. Oleic Acid
4. 11Z-C18:1 Acid
5. Linoleic Acid
6. Linolenic Acid
7. 9Z,11E-C18:2 Acid
8. 10E,12Z-C18:2 Acid
9. 9-(6-propyl-cyclohexa-2,4-dienyl)-Nonanoic Acid
10. 9Z,11E,15Z and 9Z,13E,15Z -C18:3 Acid
11. 9,11,13-C18:3 Acid 1. Palmitic Acid
2. Stearic Acid
3. Oleic Acid
4. 11Z-C18:1 Acid
5. Linoleic Acid
6. Linolenic Acid
7. 6-(6-hexyl-cyclohexa-2,4-dienyl)-hexanoic Acid
8. 9Z,11E-C18:2 Acid
9. 10E,12Z-C18:2 Acid
10. 9Z-C20:1 Acid
11. 6Z,8E,12Z-C18:3 Acid
12. 9Z-C22:1 Acid
13. 7E,9Z,11E-C18:3 Acid

CONJUGATED LINOLENIC ACIDS AND METHODS OF PREPARATION AND PURIFICATION AND USES THEREOF

This application is a U.S. National Phase under 35 U.S.C. § 371 of PCT International Application No. PCT/CA2004/001470, published in English and filed Aug. 6. 2004, which claims the benefit of Canadian Application No. 2.436,650, filed Aug. 6, 2003.

TABLE

| Nu | Fatty Acid | Trivial Name | Structure |
|---|---|---|---|
| 1 | 9Z, 12Z, 15Z-C18:3 | α-Linolenic Acid | HOOC~~~~~~~~= ~= ~= ~ |
| 2 | 6Z, 9Z, 12Z-C18:3 | γ-Linolenic Acid | HOOC~~~~= ~= ~= ~~ |
| 3 | 9Z, 12Z-C18:2 | Linoleic Acid | HOOC~~~~~~= ~= ~~~ |

FIELD OF THE INVENTION

This invention relates to the field of human and animal nutrition. More particularly, this invention relates to new conjugated linolenic acids, methods for preparing same and their use in the treatment of cancer.

BACKGROUND OF THE INVENTION

Processes for the conjugation of the double bonds of polyunsaturated unconjugated fatty acids have found their main application in the field of paints and varnishes. Oils comprised of triglycerides of conjugated fatty acids are known as drying oils. Drying oils have value because of their ability to polymerize or "dry" after they have been applied to a surface to form tough, adherent and abrasion resistant films. Tung oil is an example of a naturally occurring oil containing significant levels of fully conjugated fatty acids. Because tung oil is expensive for many industrial applications, research was directed towards finding substitutes.

In the 1930's, it was found that conjugated fatty acids were present in oil products subjected to prolonged saponification, as originally described by Moore, J. Biochem., 31: 142 (1937). This finding led to the development of several alkali isomerization processes for the production of conjugated fatty acids from various sources of polyunsaturated fatty acids.

The positioning of the double bonds in the hydrocarbon chain is typically not in a conjugated, i.e., alternating double bond single bond double bond, manner. For example, α-linolenic acid is an eighteen carbon acid with three double bonds (18:3) at carbons 9, 12 and 15 in which all three double bonds have in the cis configuration, i.e., 9Z,12Z,15Z. γ-Linolenic acid is 6Z,9Z,12Z—C18:3 acid.

Migration of double bonds (e.g., leading to conjugation) gives rise to many positional and geometric (i.e., cis-trans) isomers.

Conjugated double bonds means two or more double bonds which alternate in an unsaturated compound as in 1,3 butadiene. The hydrogen atoms are on the same side of the molecule in the case of cis structure. The hydrogen atoms are on opposite sides of the molecule in the case of trans structure.

Conjugated linoleic acid (CLA) is a general term used to name positional and geometric isomers of linoleic acid. Linoleic acid is a straight chain carboxylic acid having double bonds between the carbons 9 and 10, and between carbons 12 and 13. For example, one CLA positional isomer has double bonds between carbons 9 and 10 and carbons 11 and 12 (i.e, 9Z, 11E-C18:2 acid); another has double bonds between carbons 10 and 11 and carbons 12 and 13 (i.e., 10E,12Z—C18:2 acid), each with several possible cis and trans isomers as shown in the following Table:

Conjugated linolenic acid (CLNA) is a general term used to name positional and geometric isomers of linolenic acid. Linolenic acid is a straight chain carboxylic acid having double bonds between the carbons 9 and 10, between the carbons 12 and 13 and between carbons 15 and 16 (see the above Table).

The 9Z,11E-C18:2 isomer has been shown to be the first intermediate produced in the biohydrogenation process of linoleic acid by the anaerobic rumen bacterium *Butyrvibrio fibrisolvens*. This reaction is catalyzed by the enzyme Δ11 isomerase which converts the cis-12 double bond of linoleic acid into a trans-11 double bond. (C. R. Kepler et al., 241 J. Biol. Chem. (1966) 1350). It has also been found that the normal intestinal flora of rats can also convert linoleic acid to the 9Z, 11E-C18:2 acid isomer. The reaction does not, however, take place in animals lacking the required bacteria. Therefore, CLA is largely a product of microbial metabolism in the digestive tract of primarily ruminants, but to a lesser extent in other mammals and birds.

Conjugated Linoleic and Linolenic Acids in Cancer Therapy

The free, naturally occurring conjugated linoleic acids (CLA) have been previously isolated from fried meats and described as anticarcinogens by Y. L Ha, N K. Grimm and M. W. Pariza, in Carcinogenesis, Vol. 8, No. 12, pp. 1881-1887 (1987). Since then, they have been found in some processed cheese products (Y. L. Ha, N. K. Grimm and M. W. Pariza, in J. Agric. Food Chem., Vol. 37, No. 1, pp. 75-81 (1987)).

Conjugated Linolenic Acid (CLNA) is naturally present as a minor component of cheese from cow milk (Winkler et al., 2001) and bovine milk fat (Destaillats et al., 2003).

Cancer is a complex multifactor and multistep process involving the coordinated expression and suppression of genes functioning as positive and negative regulators of oncogenesis (Fisher, 1984; Bishop, 1991; Knudson et al., 1991; MacLachlan et al, 1995). Solid tumors are the leading cause of death attributable to cancers worldwide. Conventional methods of treating cancer include surgical treatments and the administration of chemotherapeutic agents. However, to date, such treatments have been of limited success. Chemotherapeutic treatments available today are also of limited usefulness because of their non-selective killing and/or toxicity to most cell types. Also, many tumor cells eventually become resistant against the chemotherapeutic agent, thus making treatment of solid tumors and other tumors non-feasible.

Cells can die either from apoptosis or necrosis. Unlike necrosis which is a pathological cell death, apoptosis is a death which is initially programmed in the gene of the cell itself. Thus, the gene which programs the apoptosis is activated by certain external or internal causes whereby programmed cell death gene protein is produced based upon said gene and then the cell itself is decomposed and dead by the resulting programmed death protein. Cells that undergo apoptotic cell death are characterized by a number of functional and morphologic changes: loss of membrane asymmetry, which results in the exposure of phosphatidylserine (PS) on the outer surface of cell membrane; loss of the inner mitochondrial membrane potential; activation of cytoplasmic serine proteases (caspases); rapid formation of extrusions of the cell membrane, which results in the formation of small extracellular membrane-coated particles (bleds); shrinkage of the total cell volume; condensation of the nuclear chromatin, which leads to the shrinkage of the nucleus, and fragmentation of the nucleus and the remaining cytoplasm into apoptotic bodies (Cohen, 1993).

Anti-carcinogenic properties of CLA have been well documented, as well as stimulation of the immune system. Administration of CLA inhibits rat mammary tumorogenesis, as demonstrated by Ha et al., Cancer Res., 52:2035-s (1992). Ha et al., Cancer Res., 50:1097 (1990), reported similar results in a mouse forestomach neoplasia model. CLA has also been identified as a strong cytotoxic agent against target human melanoma, colorectal and breast cancer cells in vitro. A recent major review article confirms the conclusions drawn from individual studies (Ip, Am. J. Clin. Nutr. 66(6):1523s (1997)). In in vitro tests, CLAs were tested for their effectiveness against the growth of malignant human melanomas, colon and breast cancer cells. In the culture media, there was a significant reduction in the growth of cancer cells treated with CLAs by comparison with control cultures. The mechanism by which CLAs exert anticarcinogenic activity is unknown.

In addition, CLAs have a strong antioxidative effect so that, for example, peroxidation of lipids can be inhibited (Atherosclerosis 108, 19-25 (1994)). CLA has been found to be an in vitro antioxidant, and in cells, it protects membranes from oxidative attack. In relation to other important dietary antioxidants, it quenches singlet oxygen less effectively than beta-carotene but more effectively than alpha-tocopherol. It appears to act as a chain terminating antioxidant by chain-propagating free radicals (U.S. Pat. No. 6,316,645).

Pharmaceuticals which have been used in clinical therapy include many agents such as anticancer agents, antibiotic substances, immunopotentiators, immunomodulators, etc. (such as alkylating agents antimetabolites and plant alkaloids) but it can be hardly said that such a drug therapy has been completely established already. An object of the present invention is to develop a substance having a physiological function such as apoptosis-inducing action.

Conjugated linoleic acid (CLA) is a general term used to name positional and geometric isomers of linoleic acid C18: 2(9 cis,12 cis). It usually denotes a mixture of mainly two isomers: C18:2(9cis, 11trans) and C18:2(10trans,12cis). They are usually present in a 1:1 ratio and the sum of these two isomers can vary between 30% and 90%. The majority of CLA in nutraceutical market do not mention the accurate composition for the content of each isomer, but generally the product is around 80% for both isomers. The most important isomer in term of anti-cancer activity is the C18:2(9cis, 11trans) (Seidel et al, 2001, U.S. Pat. No. 6,319,950, Liu et al., 2002, Roche et al., 2002, Pariza et al, 1991).

CLA have been suggested as useful as anti-cancer agents for treatment of cancer. The latest research reveals the most dramatic impact may be on the reduced risk and incidence of mammalian cancer (breast and colon cancer). It has been shown that CLA down-regulated mammary growth, decrease the population and proliferation activity of the cancer cells, and therefore reduces mammary cancer risk and metastasis in mice and rats (Ha et al, 1987, Ip et al, 1999). The growth inhibitory effect of CLA was also demonstrated on human breast cancer cells (Durgam et al., 1997).

Horrobin et al., in U.S. Pat. No. 6,245,811 disclosed a method for treating a disorder like complications of cancer; with compounds of structure containing group like CLA, as fatty esters as bioactive compounds Seidel et al., in U.S. Pat. No. 6,319,950 disclosed a method for the treatment of carcinoma in a human, including administering to a human a therapeutically effective amount of C18 (9-cis, 11-trans). This patent includes administering to a human a purified conjugated linoleic acid (CLA) produced by a novel synthesis process for producing C18 (9-cis, 11-trans).

Das et al., in U.S. Pat. No. 6,426,367 disclose methods of selectively reducing the blood supply to a neoplastic region, such as a tumor region, thereby selectively causing necrosis of the neoplastic tissue without substantial necrosis of adjoining tissues. The methods described in this patent employ intra-arterial injection of polyunsaturated fatty acids, such as CLA, preferably in the form of salts, preferably with a lymphographic agent, and optionally with an anti-cancer drug, and/or a cytokine.

Das et al., in U.S. Patent No. US2002077317 disclosed a method of stabilizing and potentiating the actions of 2-methoxyoestradiol, statins, H2 blockers, and C-peptide of proinsulin which have modified influence on angiogenesis and inhibiting the growth of tumor cells, as applicable by using in coupling conjugation certain polyunsaturated fatty acids (PUFAs) chosen from linoleic acid, gamma-linolenic acid, dihomo-gamma-linolenic acid, arachidonic acid, alpha-linolenic acid, eicosapentaenoic acid, docosahexaenoic acid, cis-parinaric acid or conjugated linoleic acid in predetermined quantities.

Bin et al in Patent No. CN1371985 disclosed a health-care wine containing conjugated linoleic acid or conjugated linoleic acid derivative. Said wine not only has the features of general drinking wine, but also possesses the health-care functions of resisting cancer, resisting atherosclerosis, regulating and controlling metabolism, raising immunity, regulating blood sugar and promoting growth development.

Bin et al, in Patent No. CN1356386 disclosed a process for preparing conjugated linoleic acid from dewatered castor oil includes physicochemically induced isomerizing, hydrolysis and multi-step separation. The resultant product contains conjugated linoleic acid (higher than 80%), linoleic acid (higher than 15%) and their isomers. It features its functions of preventing and treating cancer, diabetes and atherosclerosis, improving immunity, reducing blood sugar and fat.

Focant et al., in Patent No. WO02051255 relates to methods for altering the fatty acid composition in milk or tissue fat directly derived from a milk producing ruminant. In this patent methods are disclosed to obtain said desirable fatty acid profile, thereby improving the nutritional benefits to human health associated with CLA. Dietary intakes of CLA [C18:2 cis-9, trans-11] and C18:1 trans-11 fatty acids in milk or meat, or products thereof, produced in accordance with this invention in ruminant animals, can be effective in preventing cancer in different sites, reduce risk of coronary heart disease and to enhance immune function.

U.S. Pat. No. 5,554,646 (Cook et al.) discloses animal feeds containing CLA, or its non-toxic derivatives, e.g., such as sodium and potassium salts of CLA, as an additive in combination with conventional animal feeds or human foods. CLA makes for leaner animal mass.

The biological activity associated with CLAs is diverse and complex (Pariza et al. in Prog. Lipid Research., Vol 40, pp. 283-298).

Conjugated trienoic fatty acids have been suggested as useful compounds in the treatment of cell growth. Cytotoxic and anticarcinogenic effects of conjugated trienoic fatty acids have been shown on rat mammary carcinogenesis model (Futakuchi et al., 2002, Tomoyuki et al., in Patent No. JP2000336029). Same effects were observed on some lines of human tumor cells, possibly due to the induction of apoptosis of the cells (Igarashi et al., 2000a,b). In all of these studies, the authors demonstrated some properties of conjugated trienoic fatty acids, but the structure, the geometrical and positional isomers of conjugated trienoic fatty acids responsible for these effects remain to be elucidated. CLnA™ may provide potent new therapeutic molecules for the treatment of disorders such as cancers.

Tomoyuki et al, in Patent No. JP2000336029 relates to a new inhibiting agent useful in food and medicinal fields by incorporating a conjugated linolenic acid. This breast cancer-inhibiting agent contains a conjugated linolenic acid (e.g. 9,11,13-octadecatrienic acid, 10,12,14 octadecatrienic acid, their mixtures.). The breast cancer-inhibiting agent can be used not only as a medicine but also as a breast cancer-inhibiting or preventing food (e.g. a conjugated linolenic acid-containing oil and fat product), and in both cases of usage, the conjugated linolenic acid to be ingested is generally 0.01-3%, preferably 0.05-1% of the food weight.

The resemblance between the most important isomer of CLA [C18:2(9cis, 11trans)] and one of the isomers of CLnA™ [C18:3(9cis,11trans,15cis)] in term of their structure is the 9cis, 11trans insaturation. We can say that this isomer has a "CLA characteristic". The major difference between both isomers is the third insaturation: 15cis. This insaturation confers a "omega-3 fatty acid characteristic". This should increase the bioavaibility of the product and therefore increase the activity of CLnA™. The aims of the current studies are intended to demonstrate the additive effects of these two characteristics (CLA and omega-3 fatty acid in the same molecule).

Process of Preparation of Conjugated Linoleic or Linolenic Acids

All the useful methodologies for preparation of conjugated linoleic acid (CLA) were recently reviewed by Adlof (In: Yurawecz et al. (Ed), Advances in Conjugated Linoleic Acid Research, volume 1, AOCS Press, Champaign, II, pp 21-38 [1999]).

The usual methodology for conjugation of polyunsaturated fatty acids is alkali-catalyzed isomerization. This reaction may be performed using different bases such as hydroxides or alkoxides in solution in appropriate alcoholic reagents. This reaction was developed in the 1950's for spectrophotometric estimation of polyunsaturated fatty acids in fats and oils [AOCS official method Cd 7-58; JAOCS 30:352 (1953)].

In alkali isomerization the fatty acids are exposed to heat, pressure and a metal hydroxide or oxide in nonaqueous or aqueous environments, resulting in the, formation of conjugated isomers. Other methods have been described which utilize metal catalysts, which is not as efficient in the production of conjugated double bonds. It was found that isomerization could be achieved more rapidly in the presence of higher molecular weight solvent.

Kass, et al., J. Am. Chem. Soc., 61: 4829 (1939) and U.S. Pat. No. 2,487,890 (1950) showed that replacement of ethanol with ethylene glycol resulted in both an increase in conjugation in less time.

U.S. Pat. No. 2,350,583 and British Patent No. 558,881 (1944) achieved conjugation by reacting fatty acid soaps of an oil with an excess of aqueous alkali at 200-230 degrees Celsius and increased pressure.

Dehydration of methyl ricinoleate (methyl 12-hydroxy-cis-9-octadecenoate) (Gunstone and Said, Chem. Phys. Lipids 7, 121 [1971]; Berdeaux et al., JAOCS 74, 1011 [1997] give 9Z,11E-C18:2 isomer as a major product. U.S. Pat. No. 5,898,074 disclosed a synthesis process for producing this fatty acid at room temperature in high yield. The tosylate or the mesylate of the methyl ester of ricinoleic acid is formed with tosyl chloride or mesyl chloride in a pyridine solvent or in acetonitrile and triethyl amine. The obtained tosylate or mesylate is reacted with diazabicyclo-undecene in a polar, non-hydroxylic solvent of acetonitrile to form the preferred isomer of 9c,11t-18:2 methyl ester in high yield.

U.S. Pat. No. 6,160,141 disclosed a synthesis process for producing conjugated eicosanoid fatty acid from methyl lesquerolate (methyl 14-hydroxy-cis-11-octadecenoate) at room temperature in high yield using the same principle.

Among the processes known to effect isomerization without utilizing an aqueous alkali system, is a nickel-carbon catalytic method, as described by Radlove, et al, Ind. Eng. Chem. 38: 997 (1946). A variation of this method utilizes platinum or palladium-carbon as catalysts. Conjugated acids may also be obtained from a-hydroxy allylic unsaturated fatty acid using acid catalyzed reduction (Yurawecz et al., JAOCS 70, 1093 [1993]), and partial hydrogenation of conjugated acetylenic acid such as santalbic (11E-octadec-9-ynoic) acid using Lindlar's catalyst could also be used but are limited by natural sources of such fatty acid. Another approach uses strong organic bases such as butyllithium It has been applied to both the conjugation of linoleic acid and partial and full conjugation of alpha-linolenic acid ((U.S. Pat. No. 6,316,645 (Sih, et a)).

Main difference between all these procedures and the present invention is the fact that linolenic acid has three double bounds (9cis, 12cis, 15cis) that are much more reactive than the two double bonds of linoleic acid (9cis, 12cis). More precisely, the octatrienoic system (C18:3) is responsible for a sigmatropic rearrangement (see FIG. 1) that conduces to the formation of cyclic compounds (C18:3 11,13 cyclohexadiene) that are not possible to be formed during the isomerisation of the octadienoic system (C18:2). A rigorous control of the reaction kinetic's was necessary to maximize the yield of the desire mixture of isomers and minimize the amount of cyclic compounds. In fact, purification steps used in this invention are set in order to separate these cyclic compounds.

In the development of commercial compounds of linolenic acids known under the trademark CLnA™ it is important to have an inexpensive process to produce specific compositions that could be used in different formulations like nutritional bars and beverages, yoghurts, ice creams, cheese, butter, etc.

Natural fully conjugated linolenic acids have been found at high content levels in some seed oils (Hopkins, In:Gunstone, F. D. (Ed), Topics in Lipid Chemistry, volume 3, ELEK Science, London, pp 37-87 [1972]). For example, Takagi and Itabashi (Lipids 16, 546 [1981]) reported calendic acid (8E, 10E,12Z—C18:3 acid, 62.2%) in pot marigold seed oil, punicic acid (9Z,11E,13Z—C18:3 acid, 83.0%) in pomegranate seed oil, α-eleostearic acid (9Z,11E,13E-C18:3 acid) in tung (67.7%) and bitter gourd (56.2%) seed oils, and catalpic acid (9E,11E,13Z—C18:3 acid, 42.3%) in catalpa seed oil, respectively.

An octadecatrienoic acid isomer whose structure has been tentatively defined as 9Z,11E,15Z—C18:3 acid, is believed to be the first intermediate in the biohydrogenation process of α-linolenic acid by the anaerobic rumen bacterium *Butyrvibrio fibrisolvens* (C. R. Kepler and S. B. Tove 242 J. Biol. Chem. (1967) 5686).

There is thus a need to provide a process for producing at a lower cost and at a high yield conjugated linolenic acid.

There is also a need to find new conjugated fatty acids that may be easily obtained through a process for its use and the treatment of cancer.

SUMMARY OF THE INVENTION

The inventors of the present invention have surprisingly found that linolenic acids are useful in the treatment of cancer. Consequently, it would be a great benefit to propose a new process for the preparation of such molecules.

In this connection, it is an object of the present invention to provide a process for the preparation of fatty acids which are homologues of conjugated linoleic acids from natural and/or synthetic materials rich in alpha or gamma linolenic acids or both.

It is another object of the present invention to use at least one conjugated linolenic acid obtained from the process of the present invention for the prevention/treatment of cancer in a mammal.

Still another object of the present invention is to provide a composition which comprises an effective amount of 9cis, 11trans,15cis and 9cis,13trans,15cis conjugated linolenic acid isomers.

It is also an object of the present invention to use the composition of the present invention for the treatment of cancer.

The process of the present invention is unique in that the reaction produces the above-mentioned conjugated trienoic acid with a high selectivity, in a short time period and in relatively mild conditions. Again, linolenic acids obtained by the process of the present invention may be advantageously used in the treatment of cancer in a human such as breast cancer. Moreover, and as one skilled in the art will appreciate, the purification of the isomerised oil obtained by the process of this invention offers the advantage of eliminating saturated fatty acids. A further advantage of the process is the capacity to isolate an inexpensive rich fraction of cyclic compounds (C18:3 11,13 cyclohexadiene) which can be use as a synthon in Diels-Alder reactions.

DETAILED DESCRIPTION OF THE INVENTION

Figure 1:
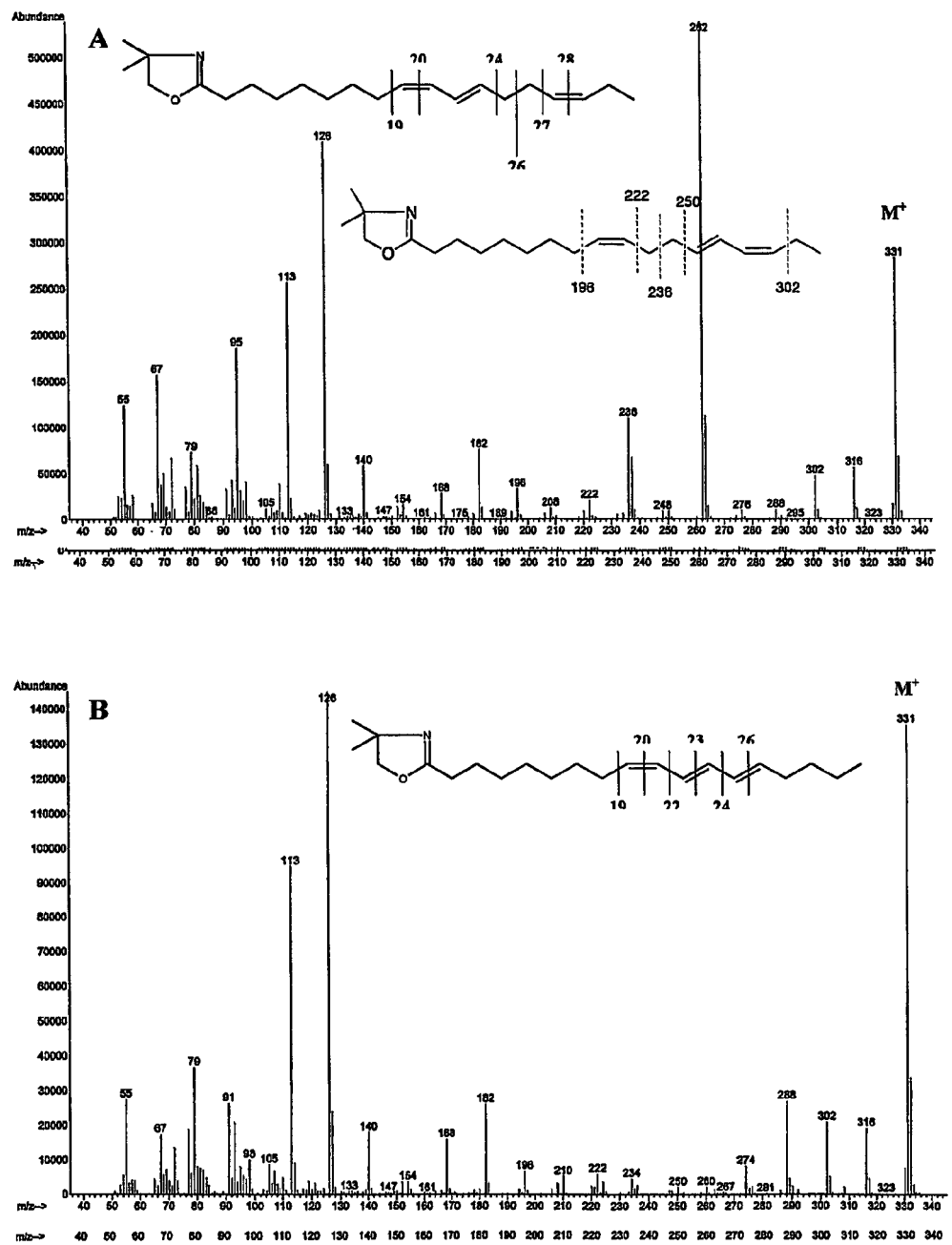
FIG. 1 presents mass spectra of products resulting from the isomerization process of alpha-linolenic acid (9Z,12Z,15Z—C18:3 acid), as 4,4-dimethyloxazoline derivatives: A, 9Z,11E,15Z and 9Z,13E,15Z—C18:3; B, 9,11,13—C18:3; C, 10E,12Z,14E-C18:3 and D, 11,13-Cyclic CLA (9-(6-propyl-cyclohexa-2,4-dienyl)-nonanoic acid)
Figure 1:
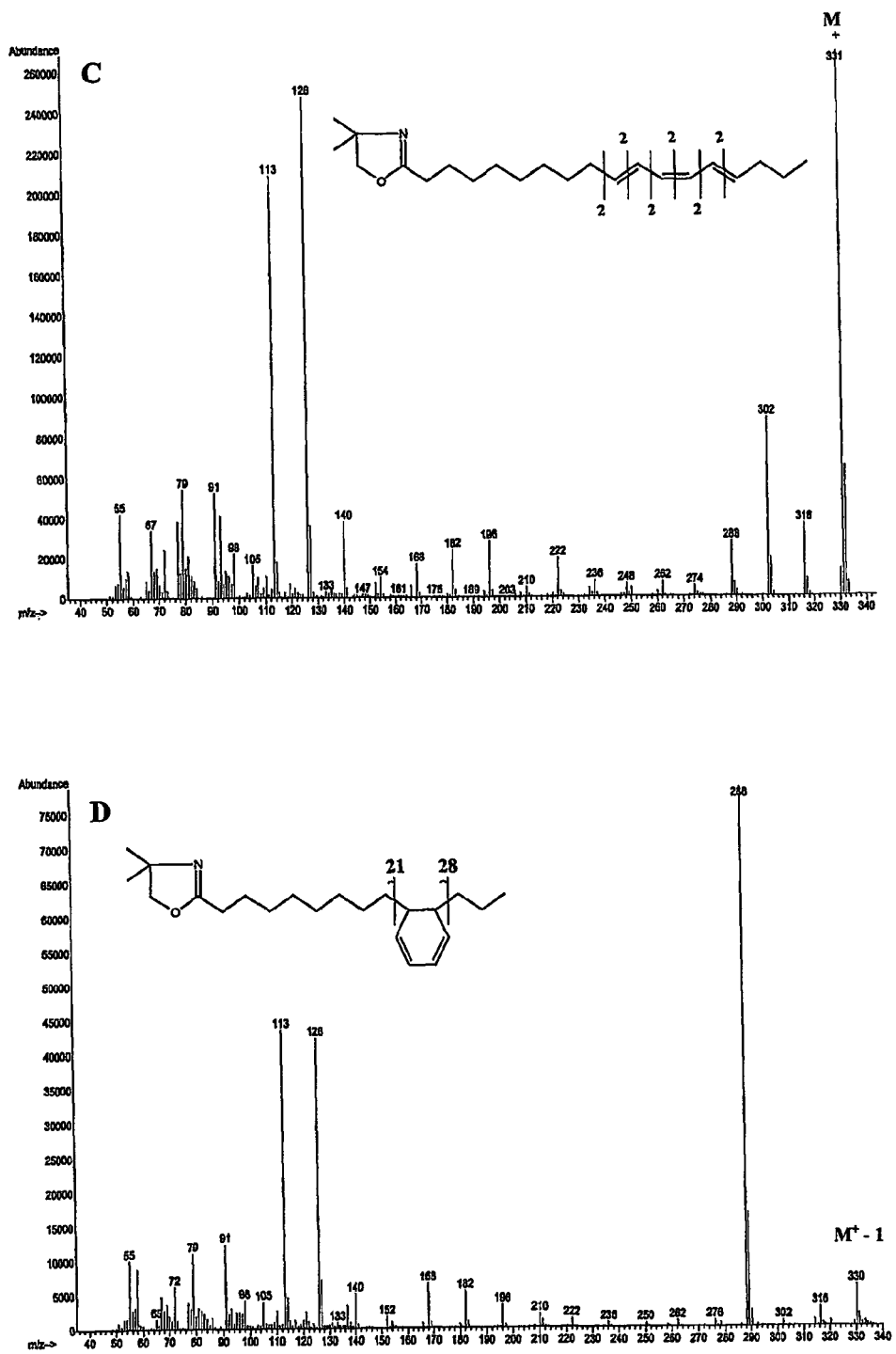

In the context of the present invention, the following terms are used and have the below described meaning.

Concerning CLA:

General term used to describe octadienoic acid systems C18:2 (18 carbons, 2 insaturations).

Commercial term used to described a 1:1 mixture of C18:2 9cis, 1 trans and C18:2 10trans, 12cis. Concentrations for the mixture may vary between 30% and 90%.

Linoleic acid (C18:2 9cis, 12cis), the major fatty acid present in different vegetal oils (sunflower, safflower, soya, corn, etc) used as starting material for CLA production. Regarding its chemical structure, it could be also considered as a CLA.

Concerning CLNA:

General term used to describe octatrienoic acid systems C18:3 (18 carbons, 3 insaturations).

Linolenic acid (C18:3 9cis, 12cis, 15cis), the major fatty acid present in different vegetal oils (linseed, basil, Plukenetia volubilis, etc) used as starting material for CLnA™ production. Regarding its chemical structure, it could be also considered as a CLNA.

Concerning CLnA™

Commercial term used by Naturia Inc. to described a 1:1 mixture of C18:3 isomers: 9cis, 11trans,15cis-octadecatrienoic acid and 9cis, 13trans,15cis-octadecatrienoic. Concentrations for the mixture may vary between 30% and 90%. Thus, the nomenclature for these products will be represented by CLnA™–30 and CLnA™–90 respectively.

Composition of Conjugated Linolenic Acids

The invention relates to the discovery of a particular mixture of isomers of conjugated linolenic acid: CLnA™ C18:3 (9cis,11trans,15cis) and C18:3(9cis,13trans,15cis). They are present in a 1:1 ratio and the sum of these two isomers may vary between 30% and 90% depending of the degree of purification.

The compositions according to the present invention contain CLnA™ which are prepared from materials rich in alpha or gamma linolenic acids like linseed oil or evening primrose oil and more particularly from a new natural source Plukenetia volubilis (Sacha Inchi or Inca Peanut), a native plant of the high altitude rain forests of the Andean region of South America. The CLnA™ may be obtained from the process of the present invention.

Process of Preparation of Conjugated Linolenic Acids

The present invention also relates to a process for preparation and purification of fatty acids which are homologues of conjugated linolenic acids, from materials rich in alpha or gamma linolenic acids. The reaction transforms between 60% and 75% of α-linolenic acid (9Z,12Z,15Z-octadecatrienoic acid) into 9Z,11E,15Z-octadecatrienoic acid and 9Z,13E, 15Z-octadecatrienoic acid. The concentration of these isomers varying from 10% to 30% in the obtained oil. Enrichment up to and over 40% is readily performed with urea crystallization. Moreover, the product can be produced in over 90% purity by simple preparative liquid chromatography. The reaction is unique in that the reaction produces the abovementioned conjugated trienoic acids with a high selectivity, in a short time period and in relatively mild conditions. The reaction also transforms gamma-linolenic acid (6Z,9Z, 12Z-octadecatrienoic acid) into 6Z,8E,15Z-octadeccatrienoic acid and 6Z,10E,12Z-octadecatrienoic. In all cases, geometrical isomers and fully conjugated isomers are also produced.

According to the present invention, only water is used as a solvent for isomerisation with a metal alkali (i.e NaOH, KOH, $Ca(OH)_2$) as catalyst. Preferred range for each reagent is as follows:

8-25% Linseed; Plukenetia volubilis oils or any other plant of the Euphorbiaceae family 70-90% Water 3-7% NaOH or KOH This process uses materials rich in alpha linolenic acid (i.e. linseed oil) or gamma linolenic acids (i.e. evening primrose oil) and more particularly a new natural source rich in alpha linolenic acid Plukenetia volubilis (Sacha Inchi or Inca Peanut), a native plant of the high altitude rain forests of the Andean region of South America.

The oils and fats, alone or as mixtures, containing alpha-linolenic acid may include but are not limited to arnebia, basil, candelnut, flax (linseed), linola, gold of pleasure, hemp, mustard, perilla, soybean, canola, walnut, chia, crambe, echium, hop, kiwi, pumkin, black currant and purslane seed oils, or any other oil, wax, ester or amide that is rich in linolenic acid.

The oils and fats, alone or as mixtures, containing gamma-linolenic acid may include but are not limited to borage, evening primrose and black currant seed oils, or any other oil, wax, ester or amide that is rich in linolenic acid.

When linseed oil is used as starting material for execution of the present invention (Table 9: assays # 0 to 8 for reaction parameters and Tables 1 to 7 for analytical results), the reaction produces approximately 30% of a 1:1 mixture of C18:3 isomers: 9cis,11trans,15cis-octadecatrienoic acid and 9cis, 13trans,15cis-octadecatrienoic; 9.5% of saturated fatty acids (5.4% palmitic and 4.3% stearic). The isomerised oil also contains 20% of unreacted oleic acid, 13% of unreacted linoleic acid (C18:2 9cis, 12cis); 4% of CLA where 1.6% accounts for C18:2 9cis, 11trans and 2.3% for C18:2 10trans, 12cis. The isomerised oil also contains 9% of unreated linolenic acid (C18:3 9cis, 12cis, 15cis). All other full conjugated C18:3 compounds accounts for 9% and the cyclic compound C18:3 11,13 ciclohexadiene accounts for 6.7%.

When Plukenetia volubilis (Sacha inchi) oil is used as starting material for execution of the present invention material (Table 9: assays 9 for reaction parameters and Table 8 for analytical results), the reaction also produces approximately 30% of a 1:1 mixture of C18:3 isomers: 9cis,11trans,15cis-octadecatrienoic acid and 9cis,13trans,15cis-octadecatrienoic. Oleic acid content (9.75%) is comparable to that obtained with linseed oil but it has less saturated fatty acids (4.16% palmitic and 3% stearic). The main difference concerns the CLA content (24%) where 11.6% accounts for C18:2 9cis, 11trans and 12.4% for C18:2 10trans, 12cis. The isomerised oil also contains 6.8% of unreacted linoleic acid (C18:2 9cis, 12cis); and only 0.38% of unreacted linolenic acid (C18:3 9cis, 12cis, 15cis). All other full conjugated C18:3 compounds accounts for 12.4% and the cyclic compound C18:3 11,13 ciclohexadiene accounts for 7.5%.

Figure 3:
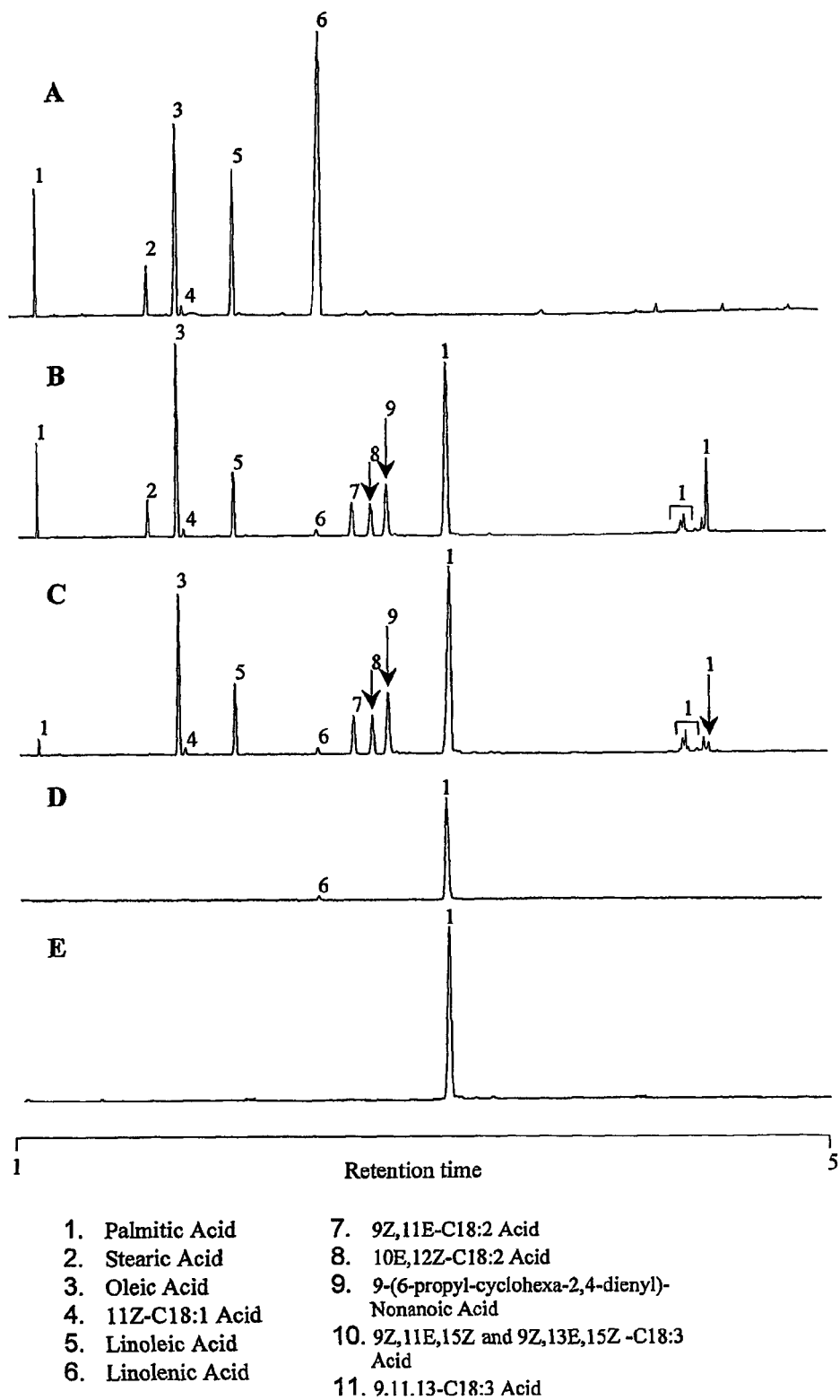
FIG. 3 presents gas liquid chromatograms of fatty acid methyl esters obtained after methylation of linseed oil (A), conjugated linseed oil (B) liquid phase from urea crystallization (C), reversed-phase liquid chromatography fraction containing about 97% of a mixture of 9Z,11E,15Z and 9Z,13E,15Z—C18:3 acids (D), argentation liquid chromatography fraction containing about 99+% of a mixture of 9Z,11E,15Z and 9Z,13E,15Z—C18:3 acids (E)
Figure 4:
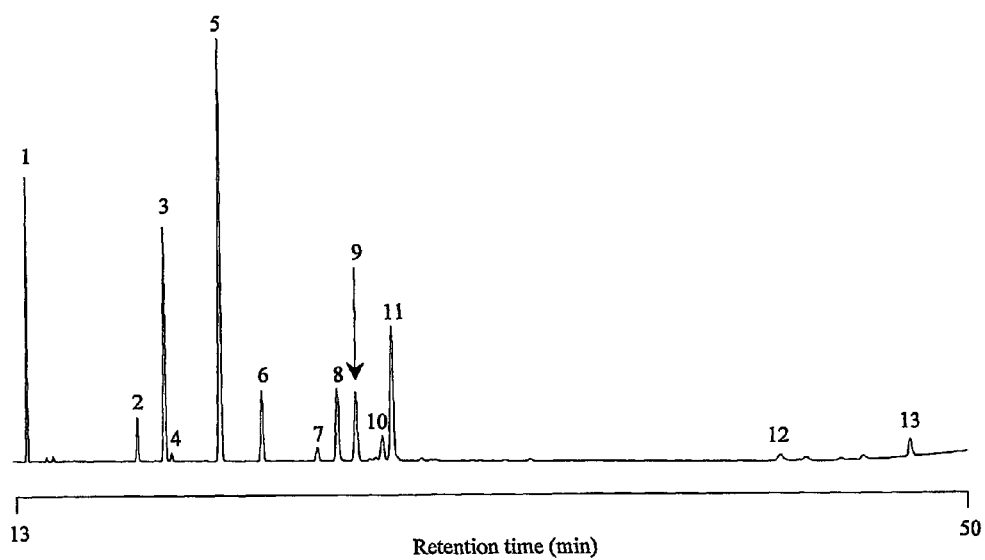
FIG. 4 presents the gas liquid chromatogram of the fatty acid methyl esters obtained after methylation of partially conjugated evening primrose oil.

In both cases, purification is performed under a rigorous control of temperature, time and the ratio between the oil, the urea and methanol. Repeatedly purification by urea crystallization enables to separate a rich fraction of cyclic compounds (67.75% in Table 10: Urea 3 Liquid fraction) and raise the concentration of the desired 1:1 mixture of C18:3 isomers to more than 75% (Table 10: Urea 4 Solid fraction). Preparative chromatography was used to purify this mixture until 90%. Gas chromatography analysis has shown the presence of both isomers (FIG. 3).

The disclosed process converts double bonds of α- and γ-linolenic acid isomers into partly and/or fully conjugated systems as well as into cyclic fatty acid isomers. The process which can be performed both in batch and continuous modes, involves blending one or a mixture of vegetable oils with various concentration of alpha or gamma linolenic acids or both or partial glycerides of such oils, or partially purified or concentrated isomers with 0.5 to 10 moles of base such as sodium hydroxide, sodium alkoxylate, sodium metal, potassium hydroxide, potassium alkoxylate, potassium metal, and strong base resins. The reaction may advantageously proceed at temperatures from 160° up to 180° C. in water as the solvent, for periods varying between 0.5 hour to 4 hours, depending on the base and/or the temperature and/or solvent, and/or substrate and/or a desire expected conversion rate (see Table 9).

After cooling, if required, to 20-80° C., acid is added to the reaction mixture to neutralize the soaps and/or remaining base in the reactor. It is preferred to bring the pH of the contents of the reactor to pH 4 or less through the addition of either a mineral or organic acid. Acids that may be used include, but are not limited to, hydrochloric acid, sulfuric acid, phosphoric acid and citric acid. The solvent phase (glycerol+water) is withdrawn and the remaining fatty acid rich phase can be washed with water and/or saline solutions of variable concentration such as sodium chloride (5% w/w) to remove traces of acids used for acidification of the reaction mixture. Remaining water can be removed by usual means (i.e. centrifugation, vacuum, distillation or drying agents). As described in Example 1, the concentration of 9Z,11E,15Z and 9Z,13E,15Z—C18:3 acid in the product is approximately 33%.

The product obtained from the process of the present invention, as such or converted into derivatives, can be used in nutrition, cosmetic, nutraceutical, biological and/or animal feed applications.

Isomer composition of the formed fatty acid was determined by gas-liquid chromatography coupled with a mass-spectrometer (GC-MS) of their 4,4-dimethyloxazoline (DMOX) derivatives. The use of derivatives is a necessary step prior to structural determination of fatty acid by GC-MS because mass spectra of fatty acid methyl ester, the usual derivatives for gas-liquid chromatography analysis, are devoid of sufficient information for identification of structural isomers. This is mainly due to the high sensitivity of the carboxyl group to fragmentation and to double bond migration (Christie, W. W., Gas Chromatography-Mass Spectrometry Methods for Structural Analysis of Fatty Acids, Lipids 33:343-353 (1998).). However, stabilization of the carboxyl group by the formation of a derivative containing a nitrogen atom results in mass spectra that allow structural determination for most fatty acids. Indeed, these fatty acids derivatives provide diagnostic fragments that allow accurate structure determination. The derivatives were submitted to GC-MS with a Hewlett Packard 5890 Series II plus gas chromatograph attached to an Agilent model 5973N MS Engine. The latter was used in the electron impact mode at 70 eV with a source temperature of 230 degree C. The GC was fitted with split injection. For DMOX derivatives an open tubular capillary column coated with BPX-70 (60 m.times.0.25 mm, 0.25 μm film; SGE, Melbourne, Australia) was used. After holding the temperature at 60 degree C. for 1 min, the oven temperature was increased by temperature-programming at 20 degree C./min to 170 degree C. where it was held for 30 min., then at 5 degree C./min to 210 degree C. where it was held for 30 min. Helium was the carrier gas at a constant flow-rate of 1 mL/min, maintained by electronic pressure control.

Mass spectrum of conjugated products of 9Z,12Z,15Z—C18:3 acid obtain by conjugation of linseed oil were presented in FIG. 1.

Structural formula and mass spectrum of the DMOX derivatives of the 9Z,11E,15Z—C18:3 acid are illustrated in FIG. 1A. The DMOX has a molecular ion at m/z=331, confirming the octadecatrienoic acid structure. The ion at m/z=262 confirms the location of the 11,15-double bond system (by extrapolation from the known 5,9-isomer (Berdeaux and Wolff, J. Am. Oil Chem. Soc., 73: 1323-1326 (1996)), similarly molecular ion at m/z=236 confirms the location of the 9,13-double bond system, and gaps of 12 a.m.u. between m/z=208 and 196, and 288 and 276 verify the location of double bonds in positions 9 and 15, respectively. Mass spectrometry does not confirm the geometry of the double bonds, but they have been determined according to Nichols et al. (J. Am. Chem. Soc, 73:247-252 (1951)) based on the Ingold theory on the prototropic shift mechanism (Ingold, J. Chem. Soc, 1477 (1926)).

Structural formula and mass spectrum of the DMOX derivatives of the 9,11,13—C18:3 acid are illustrated in FIG. 1B. The DMOX has a molecular ion at m/z=331, confirming the octadecatrienoic acid structure. Gaps of 12 a.m.u. between m/z=208 and 196, and 222 and 234, and 248 and 260 verify the location of double bonds in positions 9, I1 and 13, respectively. Four different minor isomers of 9,11,13—C18:3 are present in the reaction products. The most abundant is the 9Z,11Z,13E-C18:3 acid isomer which is known as α-eleostearic acid.

Figure 2:
FIG. 2 presents the thermal mechanism leading to the formation of 11,13-Cyclic CLA [9-(6-propyl-cyclohexa-2,4-dienyl)-nonanoic acid (FIG. 1-D)] from 10E,12Z,14E-C18:3 acid.

Mass spectra of the MTAD adducts of cis-9,trans-11,cis-15 18:3 (A) and cis-9, trans-13,cis-15 18:3 (B) acid methyl esters and presented at FIG. 2.

Structural formula and mass spectrum of the DMOX derivatives of the 10E,12Z,14E-C18:3 acid are illustrated in FIG. 1C. The DMOX has a molecular ion at m/z=331, confirming the octadecatrienoic acid structure. Gaps of 12 a.m.u. between m/z=210 and 222, and 236 and 248, and 262 and 274 verify the location of double bonds in positions 10, 12 and 14, respectively. Mass spectrometry does not confirm the geometry of the double bonds, but they have been determined according to Nichols et al. (J. Am. Chem. Soc, 73:247-252 (1951)) based on the Ingold theory on the prototropic shift mechanism (Ingold, J. Chem. Soc, 1477 (1926)). The 10E, 12Z,14E-C18:3 acid isomer is prone to cyclization, thus forming cyclohexadienyl compound (9-(6-propyl-cyclohexa-2,4-dienyl)-nonanoic acid)) by an electrocyclization process presented in FIG. 3.

Structural formula and mass spectrum of the DMOX derivatives of the 11,13-Cyclic CLA (9-(6-propyl-cyclohexa-2,4-dienyl)-nonanoic acid) are illustrated in FIG. 1D. The DMOX has a molecular ion at m/z=330−1, confirming the occurrence of a high stabilized conjugated ion fragment (radical in carbon 10 or 15, stabilized by resonance effect). A distinctive ion at m/z=288 is characteristic for alpha cleavage occurring in cyclic fatty acids (Sébédio et al. J. Am. Oil Chem. Soc., 64: 1324-1333 (1987)). The gap of 78 atomic mass units (a.m.u.) between m/z=288 and 210 is that expected for the cyclohexadienyl group which conjugated double bond system in positions 11 and 13.

Reaction progress was determined by gas-liquid chromatography under appropriate condition as presented in EXAMPLE 1.

Increasing the concentration of, for example 9Z,11E, 15Z and 9Z, 13E, 15Z—C18:3 acids, can be achieved using different methods, alone or in combination. One method makes use of urea complexation. Urea solution, prepared at a temperature ranging from 20 to 90° C. in different solvents or mixtures thereof, selected from water, and/or alcohols. Complexation is performed at the same temperature by addition of the product in a molar ratio of 0.5 to 8, and cooling at a temperature range of 20 to −10° C., as required. A mixture of the abovementioned 9Z,11E,15Z and 9Z,13E,15Z—C18:3 acids is isolated in higher concentration after treatment of the liquid phase, obtained after separation from the solid phase, by using conventional means such as filtration or centrifugation. Decomplexation is then carried out by addition of either a diluted organic or mineral acid. Acids that may be used include, but are not limited to, hydrochloric acid, sulfuric acid, phosphoric acid and citric acid. The product is obtained by decantation or liquid-liquid extraction with an organic solvent such as but not limited to hexane, heptane, petroleum ether and ligroin. If required, the organic solvent is eliminated (i.e. evaporated or distilled). A preferred description of the present embodiment is described in Example 2.

Another method for raising level of, for example 9Z,11E, 15Z and 9Z,13E,15Z—C18:3 acids, either as free acid or derivative (i.e. methyl, ethyl, isopropyl, butyl, phenyl) is liquid chromatography using various convenient stationary phases. One particular is reversed phase liquid chromatography (i.e. ODS) for which eluents may include but are not limited to water, acetonitrile, acetone, methanol, tetrahydrofuran, methyl-tertbutyl ether, and combination thereof. A detailed description of the method is described in Example 3. Argentation liquid chromatography may be used to isolate specific isomers from a complex mixture of fatty acid ester or free fatty acid. A detailed description of the methodology applied to a mixture of 9Z,11E,15Z and 9Z,13E,15Z—C18:3 acid isomers is described in Example 4.

Still another method for raising the concentration level of, for example a mixture of 9Z, 11E,15Z and 9Z,13E,15Z—C18:3 acid, either as free acid or derivative (i.e. methyl, ethyl, isopropyl, butyl, phenyl) is crystallization, either in solvent or mixture thereof, such as, but not limited to, acetone, methanol, pentane, or in absence of solvent (i.e. dry fractionation). A detailed cooling program is required in order to obtain a more concentrated product. One particular case is that of further crystallization of urea complexes of fatty acids.

Purification of the isomerised oil by urea crystallization enables to separate many different fractions one of them rich in cyclic compounds (68%) and other with the desired 1:1 mixture of C18:3 isomers (75%). Preparative chromatography was used to purify this mixture until 90%.

Conjugated Linolenic Acids in Cancer Therapy/Prevention

The present invention also concerns the use of linolenic acids in the prevention and treatment of cancer. Indeed, the inventors have discovered that linolenic acids induce cytotoxicity of human cancer cells by apoptosis. The method of the present invention provides for the treatment of cancer in a human, including the treatment of mammary cancer. The method of the present invention provides cytotoxicity of cancer cells using CLnA™. CLnA™ has a significant potency relative to other fatty acids in respect to an ability to modulate tumorigenesis.

The compounds obtained from the process of the present invention are useful for the treatment of human cancer cells. In particular, the compounds of the invention have been found to be potent inhibitors of tumor cell proliferation and survival, and effective to induce apoptosis of malignant human cells. Compounds of the invention have been found to be effective for inducing cytotoxicity and/or apoptosis of human breast cancer cells.

The invention may be further clarified by reference to the following Examples, which serve to exemplify some of the preferred embodiments, and not to limit the invention in any way.

EXAMPLES

I Process of Preparing Linolenic Acids

The following examples are provided in order to demonstrate and further illustrate certain preferred embodiments and aspects of the present invention. It should be understood that the invention as claimed should not be limited to such specific embodiments. Modifications of the described process for those skilled in the art are intended to be within the scope of the present invention.

In the experimental disclosure which follows, the following abbreviations apply: Kg (kilograms); g (grams); mg (milligrams); ° C. (degrees centigrade); L (liters); mL (milliliters); µL (microliters); m (meters); cm (centimeters); mm (millimeters), µm (micrometers); NaOH (sodium hydroxide), $H_2SO_4$ (sulfuric acid), NaCl (sodium chloride); C18:2 11,13 cyclohexadiene (cyclic compounds).

Example 1

Linseed Oil Isomerization in Propylene Glycol

In a preferred embodiment 378 gr of NaOH were dissolved in 7778 kg of propylene glycol at 160 C in a 25 L stainless steel reactor with a condenser. When dissolution was completed (30 min) 712 g of linseed oil were loaded under vacuum and nitrogen was use to reestablish the atmospheric pressure. The reaction was performed under nitrogen atmosphere at 160° C. during 2 hours. (Table 9: Assay #0). After what, the mixture was cooled to 25° C. and pH was adjusted to 3 with 460 g of concentrated $H_2SO_4$ dissolved in 7.61 Kg of water. After 15 minutes decantation the aqueous phase was removed and 45 Kg of water were added to the reactor to wash the isomerized fatty acid oily phase. After another 15 min decantation the washing water was removed to obtain 655 g of the isomerized linseed oil that was analyzed by gas chromatography by the method previously described. The fatty acids profile for the isomerized product is described in Table 1 at the column "Propylene glycol". It has 30.94% of a 1:1 mixture of C18:3 isomers: 9cis,11trans,15cis-octadecatrienoic acid and 9cis,13trans,15cis-octadecatrienoic. Under our nomenclature it is named CLnA™-30. As a reference, the column "Linseed oil" in Table 1 presents the fatty acids profile of this particular starting material. It is clear that almost all the 53.53% of the linolenic acid (C18:2 9cis, 11cis, 15cis) present in linseed oil was reacted (only 0.22% was not reacted) to produce 30.94% of the desired mixture, 8.32% of the cyclic compounds, and 11.57% of full conjugated C18:3 isomers. Regarding the distribution of C18:3 isomers the corresponding yields of conversion were: 60.87%, 13.67% and 22.76% respectively.

First urea crystallization was performed over the 655 g of CLnA™-30 obtained in the saponification/isomerization step. A methanolic-urea solution was prepared by dissolving 1.3 Kg of urea with 4.140 Kg of methanol at reflux temperature in a stainless steel reactor. Once all the urea dissolved, 655 g of CLnA™-30 were added to the reactor under agitation. The reaction mixture was cooled until 25° C. in 10 minutes and then cooled to 25° C. in 10 hours. After what the urea adduct was filtrated over a previously cooled centrifuged to separate a solid and a liquid fractions. The liquid phase was decomplexed by addition of 98 g of concentrated $H_2SO_4$ dissolved in 10.6 Kg of water (approximately a 1% w/w $H_2SO_4$ solution). After decantation, the aqueous phase was removed and the oily phase washed with a 5% w/w NaCl aqueous solution (270 gr of NaCl in 5.12 Kg of water) to obtain 393 g of $1^{st}$ purified isomerized linseed oil. The product was analyzed by gas chromatography by the method previously described.

The composition of the Urea 1 Liquid (U1L) product was shown in Table 10 at the column U1L ($1^{st}$ column shadowed). The concentration of the desired 1:1 mixture of C18:3 isomers: 9cis, 11trans, 15cis-octadecatrienoic acid and 9cis, 13trans,15cis-octadecatrienoic was 39.96%. Under our nomenclature it is named CLnA™-40.

Second urea crystallization was performed over the 393 g of CLnA™-40 obtained in the $1^{st}$ urea crystallization step (U1L). A methanolic-urea solution was prepared by dissolving 1.572 Kg of urea with 4.97 Kg of methanol at reflux temperature in a stainless steel reactor. Once all the urea dissolved, 393 g of CLnA™-40 were added to the reactor under agitation. The reaction mixture was cooled until 25° C. in 10 minutes and then cooled to 25° C. in 8 hours. After what the urea adduct was filtrated over a previously cooled centrifuged to separate a solid and a liquid fractions. The liquid phase was decomplexed by addition of 29.4 g of concentrated $H_2SO_4$ dissolved in 3.166 Kg of water (approximately a 1% w/w $H_2SO_4$ solution). After decantation, the aqueous phase was removed and the oily phase washed with a 5% w/w NaCl aqueous solution (162 gr of NaCl in 2.76 Kg of water) to obtain 236.4 gr of $2^{nd}$ purified isomerized linseed oil. The product was analyzed by gas chromatography by the method previously described.

The composition of the Urea 2 Liquid (U2L) product was shown in Table 10 at the column U2L ($2$nd column shadowed). The concentration of the desired 1:1 mixture of C18:3 isomers: 9cis, 11 trans,15cis-octadecatrienoic acid and 9cis, 13trans, 15cis-octadecatrienoic was 45.4%. Under our nomenclature it is named CLnA™-45.

Third urea crystallization was performed over the 236.4 g of CLnA™-45 obtained in the $2^{nd}$ urea crystallization step (U2L). A methanolic-urea solution was prepared by dissolving 946 g of urea with 2.9 Kg of methanol at reflux temperature in a 5 L three necked-flask. Once all the urea dissolved, 236.4 g of CLnA™-45 were added to the flask under agitation. The reaction mixture was cooled until 25° C. in 10 minutes and then cooled to 25° C. in 6 hours. After what the urea adduct was filtrated over a previously cooled büchner to separate a solid and a liquid fractions. The solid phase was decomplexed by addition of 17.71 g of concentrated $H_2SO_4$ dissolved in 19 Kg of water (approximately a 1% wow $H_2SO_4$ solution). After decantation, the aqueous phase was removed and the oily phase washed with a 5% w/w NaCl aqueous solution (97.3 gr of NaCl in 1.85 Kg of water) to obtain 28.5 g of $3^{rd}$ purified isomerized linseed oil. The product was analyzed by gas chromatography by the method previously described.

The composition of the Urea 3 Solid (U3S) product was shown in Table 10 at the column U3S ($3^{rd}$ column shadowed). The concentration of the desired 1:1 mixture of C18:3 isomers: 9cis,11trans,15cis-octadecatrienoic acid and 9cis, 13trans,15cis-octadecatrienoic was 72.34%. Under our nomenclature it is named CLnA™-70.

Fourth urea crystallization was performed over the 28.5 g of CLnA™-70 obtained in the $3^{rd}$ urea crystallization step (U3S). A methanolic-urea solution was prepared by dissolving 57 g of urea with 180 g of methanol at reflux temperature in a 500 mL three necked-flask. Once all the urea dissolved, 28.5 g of CLnA™-70 were added to the erlenmeyer under agitation. The reaction mixture was cooled until 25° C. in 10 minutes and then cooled to 25° C. in 6 hours. After what the urea adduct was filtrated over a previously cooled büchner filter to separate a solid and a liquid fractions. The solid phase was decomplexed by addition of 2.13 g of concentrated $H_2SO_4$ dissolved in 230 g of water (approximately a 1% w/w $H_2SO_4$ solution). After decantation, the aqueous phase was removed and the oily phase washed with a 5% w/w NaCl aqueous solution (11.7 g of NaCl in 222.6 g of water) to obtain 21.36 g of $4^{th}$ purified isomerized linseed oil. The product was analyzed by gas chromatography by the method previously described.

The composition of the Urea 4 Solid (U4S) product was shown in Table 10 at the column U4S ($4^{th}$ column shadowed). The concentration of the desired 1:1 mixture of C18:3 isomers: 9cis,11trans,15cis-octadecatrienoic acid and 9cis, 13trans,15cis-octadecatrienoic was 75.35%. Under our nomenclature it is named CLnA™-75.

Example 2

Linseed Oil Isomerization in Water

In a preferred embodiment 666 g of NaOH were dissolved in 15.794 kg of water at 80 C in a 25 L stainless steel reactor with a condenser. When dissolution was completed (30 min) 1.428 Kg of linseed oil were loaded under vacuum and nitrogen was use to reestablish the atmospheric pressure. The reaction was performed under nitrogen atmosphere at 170° C. during 3 hours. (Table 9: Assay #2). After what, the mixture was cooled to 60° C. and a stoichiometric amount of $CaCl_2$ was added under very low agitation. The sodium soaps were transformed into calcium soaps and they precipitate while the sodium chloride formed is solubilized in the aqueous phase (FIG. 2). Calcium soaps of isomerized linseed oil were separated by filtration over a centrifuge and washed with water. The washed calcium soaps were transferred to another reactor containing a stoichiometric amount of $H_2SO_4$ in methanol. Acidification until pH 3 produces a white precipitate of $CaSO_4$ that was separated by filtration over a Sparkler filter. The solution contains the free fatty acids of the isomerized linseed oil with the composition described in Table 2 after 3 hours reaction. The isomerized oil contains 29.64% of a 1:1 mixture of C18:3 isomers: 9cis,11trans,15cis-octadecatrienoic acid and 9cis,13trans,15cis-octadecatrienoic. Under our nomenclature it is named CLnA™-30. As a reference, the column "Linseed oil" in Table 2 also presents the fatty acids profile for this starting material. It can be noted that 10% of the linolenic acid (C18:2 9cis, 11cis, 15cis) present in linseed oil was not reacted. The other fatty acids contained in the isomerized oil are: 6.47% of the cyclic compounds, and 6.69% of full conjugated C18:3 isomers. The content of CLA (3.02%) is distributed by 1.66% of C18:2 9cis, 11trans and 2.06% of C18:2 10trans, 12cis. Most of the linoleic acid (C18:2 9cis, 12cis) remains unreacted (13.12%). The nomenclature for the isomerized oil correspond to CLnA™-30 and the purifications steps with this corresponding yields and concentrations (via repetitive urea crystallizations) are similar to those used and obtained in Example 1.

Example 3

*Plukenetia volubilis* Oil Isomerization in Water

In a preferred embodiment 1.22 Kg of NaOH were dissolved in 15.508 Kg of water at 80 C in a 25 L stainless steel reactor with a condenser. When dissolution was completed (30 min) 491 g of *Plukenetia volubilis* oil were loaded under vacuum and nitrogen was use to reestablish the atmospheric pressure. The reaction was performed under nitrogen atmosphere at 180° C. during 4 hours. (Table 9: Assay #9). After what, the mixture was cooled to 60° C. and a stoichiometric amount of $CaCl_2$ was added under very low agitation. The sodium soaps were transformed into calcium soaps and they precipitate while the sodium chloride formed is solubilized in the aqueous phase (FIG. 2). Calcium soaps of isomerized *Plukenetia volubilis* oil were separated by filtration over a centrifuge and washed with water. The washed calcium soaps were transferred to another reactor containing a stoichiometric amount of $H_2SO_4$ in methanol. Acidification until pH 3 produces a white precipitate of $CaSO_4$ that was separated by filtration over a Sparkler filter. The solution contains the free fatty acids of the isomerized *Plukenetia volubilis* oil with the composition described in Table 8. The isomerized oil contains 30.08% of a 1:1 mixture of C18:3 isomers: 9cis,11trans, 15cis-octadecatrienoic acid and 9cis,13trans,15cis-octadecatrienoic. Under our nomenclature it is named CLnA™-30. As a reference, the column "Linseed oil" in Table 8 also presents the fatty acids profile for this starting material. It is clear that almost all the 51.82% of the linolenic acid (C18:2 9cis, 11cis, 15cis) present in *Plukenetia volubilis* oil was reacted (only 0.38% was not reacted) to produce 30.08% of the desired mixture, 7.58% of the cyclic compounds, and 12.41% of full conjugated C18:3 isomers. Regarding the distribution of C18:3 isomers the corresponding yields of conversion were: 60.08%, 15.14% and 24.79% respectively. Almost the same fatty acids profile of the Example 1. The main difference concerns the much significant quantity of CLA (24%) where 11.6% accounts for C18:2 9cis, 11trans and 12.4% for C18:2 10trans, 12cis. %). The nomenclature for the isomerized oil correspond to CLnA™-30 and the purifications steps with this corresponding yields and concentrations (via repetitive urea crystallizations) are similar to those used and obtained in Example 1.

Example 4

Preparation and Purification of 9Z,11E,15Z and 9Z,13E,15Z—C18:3 Acids by Argentation Liquid Chromatography Fatty acid methyl esters prepared from products obtained in example 1 and 2 that containing a high level of a mixture of 9Z,11E,15Z and 9Z,13E,15Z—C18:3 were separated using argentation thin layer chromatography. Silica-gel plates were prepared by immersion in a 5% acetonitrile solution of $AgNO_3$ as described by Destaillats et al. (Lipids 35:1027-1032, (2000)). The developing solvent was the mixture n-hexane/diethyl ether (90:10, v/v). At the end of the chromatographic runs, the plates were briefly air-dried, lightly sprayed with a solution of 2',7'-dichlorofluorescein, and viewed under ultraviolet light (234 nm). The band at $R_f$=0.52 was scraped off and eluted several times with diethyl ether. Complete evaporation of the combined extracts was achieved with a light stream of dry nitrogen. The residues were dissolved in an appropriate volume of n-hexane and analysed by gas-liquid chromatography (purity superior to 98%) as presented in example 1.

II Use of Linolenic Acids in Cancer Therapy

The invention relates to the discovery that CLnA™ compounds induce apoptosis of cancer cells. The activity of CLnA™ was demonstrated in two human breast cancer lines (breast cancer cells MCF-7 and MDA-MB-231), using MTT assay and fluorescence-based assay. Our results suggest that CLnA™ has a cytotoxic activity and induce apoptosis in human solid tumors cells lines. Therefore may be used for the treatment of cancer, including advanced cancer.

Example 1

Cytotocixity of CLA and CLnA™ Compounds

The cytotoxicity of the CLA and CLnA™ compounds against two human tumor cells lines was evaluated. The CLA was purchased from Sigma Aldrich and CLNA™ compounds were prepared as described in previous examples. The detailed composition of each one is presented in Table 11. They were tested, along with 1% (v/v) of ethanol in culture medium as a control.

1. Cell Culture

Human cell lines were obtained from American Type Culture Collection (ATCC, Rockville, Md.). Cells used in this study include estrogen receptor negative human breast cancer cells MDA-MB-231 and estrogen receptor positive MCF-7. They are cultured in a humidified 5% $CO_2$ atmosphere, at 37 degree C. Cells were maintained as a continuous cell line in Modified Eagles' medium supplemented with 10% fetal bovine serum, and antibiotics.

MTT Proliferation Assay

The cytotoxicity of various compounds against human tumor cell lines was performed using the MTT (3-[4,5-dimethylthiazol-2-yl]-2,5-diphenyl tetrazolium bromide) assay (Sigma Chemical Co., St. Louis, Mo.). Briefly, exponentially growing tumor cells were seeded into a 96-well plate at a density of 1500 cells/well and incubated for 4 hours at 37° C. prior to drug exposure. For the treatment, culture medium was carefully aspirated from the wells and replaced with fresh medium containing the vehicle (ethanol 1%, (volume in culture medium), CLA or CLnA™ compounds at concentrations ranging from 10 to 100 μM. Fatty acids were complexed to bovine serum albumin (BSA) 1 h at 37° C. with agitation, prior to be added to the cells. Triplicate wells were used for each treatment. The cells were incubated with the various compounds for 24-96 hours at 37° C. in a humidified 5% $CO_2$ atmosphere.

After incubation, cell survival was determined using a tetrazolium (MTT)-based calorimetric assay (Mosmann, et al., 1983). Briefly, MTT assay mesure the cell proliferation related to the mitochondrial activity. In a viable cells, there are active mitochondrias that reduce the yellow compound MTT in a blue compound. To each well, 100 μL of MTT (0.5 mg/ml final concentration in phosphate buffered saline) was added and the plates were incubated at 37° C. for 4 hours in a humidified 5% $CO_2$ atmosphere to allow MTT to form formazan crystals by reacting with metabolically active cells. The formazan crystals were solubilized in a solution containing 10% SDS in 0.01 M HCL, for 3 h at 37° C. in a humidified 5% $CO_2$ atmosphere. The optical absorbance of each well was measured in a microplate reader spectrophotometer (Synergy HT, Biotek) at 570 nm and a reference wavelength of 630 nm. The percent cytotocixity was calculated using the formula: 1−(x570/xctrl)×100. Each experiment was done in triplicate and repeated 3 times.

Detection of Apoptosis and Necrosis by Fluorescence-Based Microplate

Exponentially growing cells were seeded in 96-well tissue culture plates at a density of 1500 cells/well and cultured for 36 hours at 37° C. in a humidified 5% $CO_2$ atmosphere. The supernatant culture medium was carefully aspirated and replaced with fresh medium containing the vehicle (ethanol 1% v/v), CLA or CLnA™ compounds at concentrations ranging from 10 to 100 µM. After incubation, apoptosis and necrosis was determined by adding fluorescence markers of cell death: 50 µL of staining solution (YO-PRO-1 5 µg/mL and PI 20 µg/mL, Molecular Probes) is added to each well. YO-PRO-1 is a specific dye for apoptotic cells while propidium iodide (PI) is a specific dye for necrotic cells. YO-PRO-1 dye is permeant to apoptotic cells, providing a convenient indicator of apoptosis. There is selective uptake of YO-PRO-1 by apoptotic cells. YO-PRO-1 nucleic acid stain selectively passes through the plasma membranes of apoptotic cells and labels them with green fluorescence. Necrotic cells are stained with the red-fluorescent PI, a DNA-selective dye that is membrane impermeant but that easily passes through the compromised plasma membranes of necrotic cells. Live cells are not stained by either YO-PRO-1 or PI. Plates were then incubated in dark for 30 min on ice. Fluorescence was measured with a microplate spectrophotometer (Synergy HT, Biotek). Each experiments was done in triplicate and repeated 3 times.

Detection of Apoptosis and Necrosis by Fluorescence Microscopy

In brief, 10×5 cells/ml were grown for 48 h on glass coverslips placed in 6-well plates with media containing 100 µM CLnA™ or ethanol 1% as control. Cells were washed twice with binding buffer (10 mM HEPES, 140 mM NaCl, 2.5 mM $CaCl_2$, pH 7.4). Cells were then incubated in the dark with annexin V conjugated to fluorescein isothiocyanate (FITC, Molecular Probes) and 0.20 µg/ml PI for 20 min at room temperature. After washing twice the cells with buffer, the coverslips were mounted onto slides with Vectashield (Vector Labs, Burlingame, Calif.) and viewed with a fluorescence microscope. Cells were visualized and photographed at a primary magnification of 40 times. Each experiments was done in triplicate and repeated 3 times.

A characteristic of apoptotic cells is the translocation of PS residues, that are normally confined to the inner leaflet of the plasma membrane, to the outer leaflet (Martin et al., 1995). This plasma membrane change can be efficiently detected by the use of FITC-conjugated annexin V, a protein with extremely high affinity for binding to PS, and observation of cells by fluorescence microscopy. FITC-labeled annexin V was used to bind exposed PS on cells undergoing the early stages of apoptosis. Annexin V will selectively bind these exposed PS. PI is membrane impermeant and bind to DNA by intercalating between bases. PI also binds to RNA. Once the dye is bound to nucleic acids, its fluorescence is enhanced. PI is excluded from viable cells and fluoresces red in the presence of DNA. In the color photographs, red fluorescence represents nuclei stained with PI. Green or yellow (e.g. superimposed red plus green) represents the apoptotic cells. Non-apoptotic cells do not incorporate significant amounts of PI, and consequently have much less fluorescence than apoptotic cells. Using a combination of these fluochromes it was possible to distinguishes between viable cells (do not incorporate neither annexin V nor PI), early apoptotic (green fluorescence), late apoptotic (green fluorescence with red fluorescence) and necrotic cells (red fluorescence).

Results

Effect of CLA and CLnA™ on Proliferation of Human Breast Cancer Cell Lines

Figure 5:
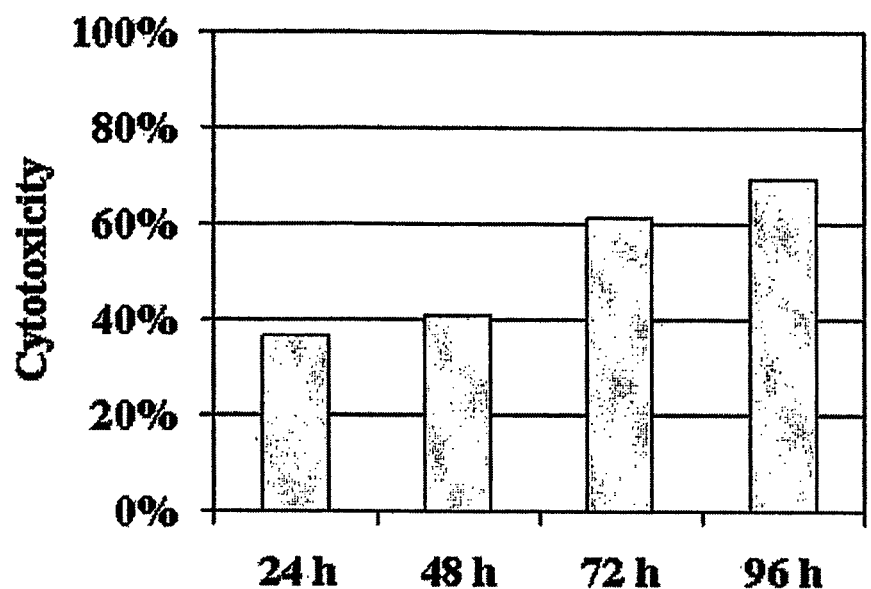
FIG. 5: Cytotoxicity of CLA (100 μM) on MDA-MB-231 cells. Cells were exposed to 100 μM CLA for different periods of time. Cytotoxicity was determined by calorimetric MTT cell proliferation assay as described in Methods. Results are shown as mean of triplicate experiments. This is one of the representative results of 3 independent experiments.

Two human breast cancer cell lines, the MDA-MB-231 and MCF-7 were treated with CLA or CLnA™ at concentrations of 10 to 100 µM for 24 to 96 hours or with ethanol 1% (v/v) as a control. Our results demonstrated that when MDA-MB-231 cells were incubated with CLA 100 µM for different period of time, there is an increase in the cytotocixity of the cells (FIG. 5). After 96 h, about 70% of cell death.

Figure 6:
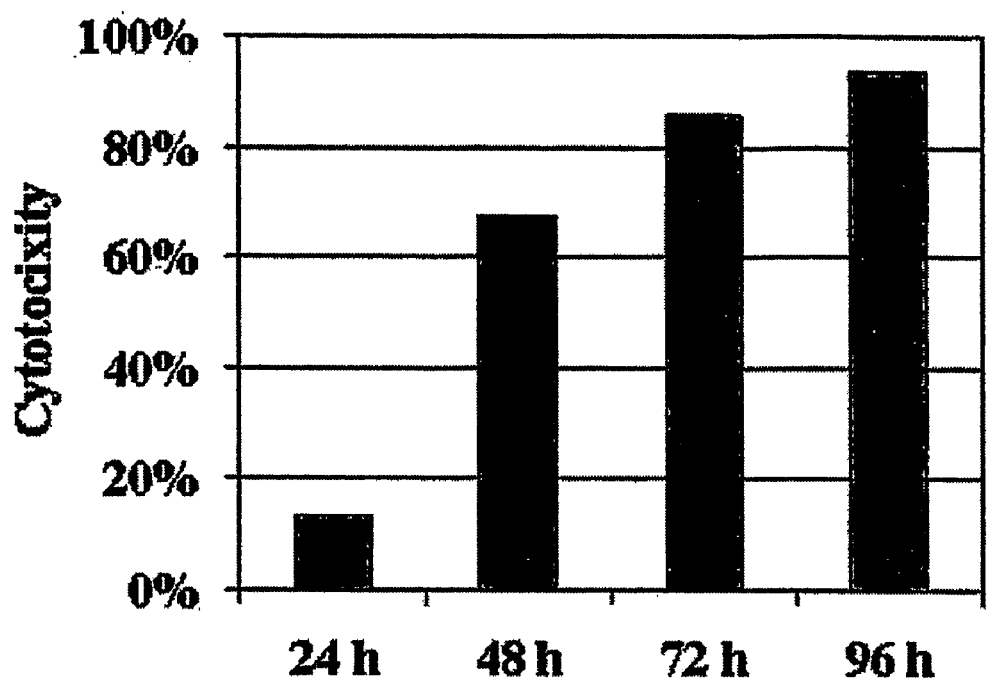
FIG. 6: Cytotoxicity of CLnA™ (100 μM) on MDA-MB-231 cells. Cells were exposed to 100 μM CLnA™ for different periods of time. Cytotoxicity was determined by calorimetric MTT cell proliferation assay as described in Methods. Results are shown as mean of triplicate experiments. This is one of the representative results of 3 independent experiments.

When the MDA-MB-231 cells were treated with CLnA™ 100 µM, there is also an increase in the cytotocixity of the cells. After 96 h, almost all the cancer cell are dead. (FIG. 6). The same results were also observed on MCF-7 cells. From these results, we can conclude that CLnA™ is more cytotoxic on human cancer cell than CLA.

Figure 7:
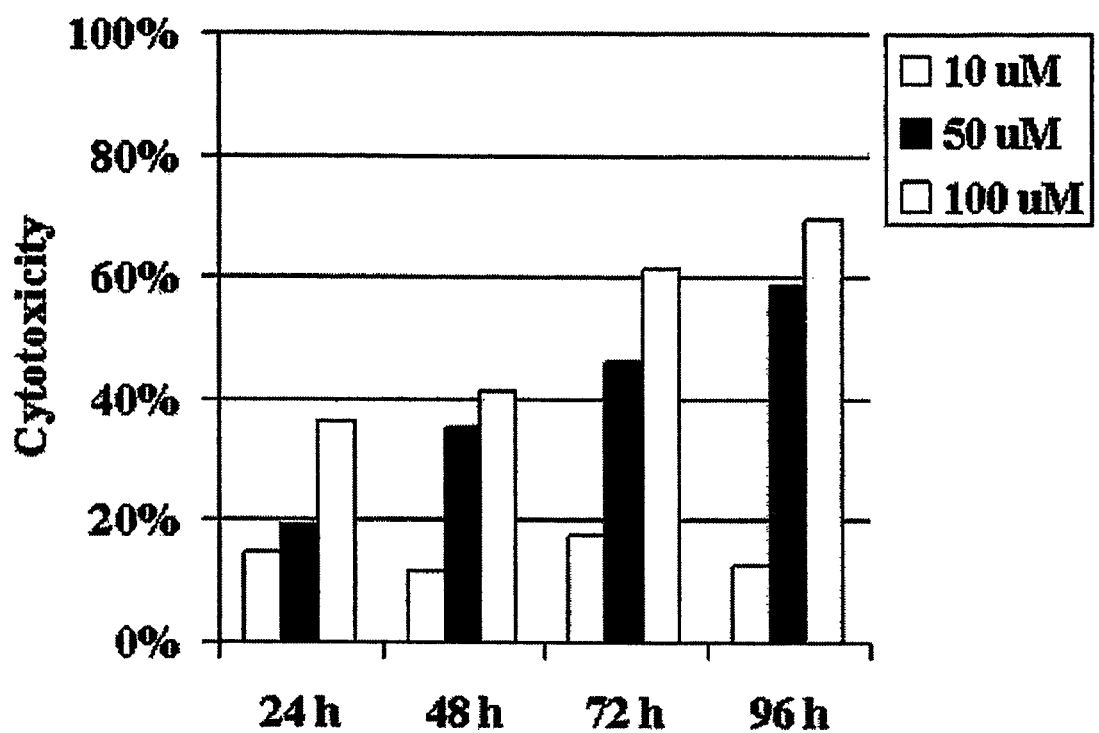
FIG. 7: Cytotoxicity dose-dependant of CLA on MDA-MB-231 cells. Cells were exposed to different concentrations of CLA for different periods of time. Cytotoxicity was determined by colorimetric MTT cell proliferation assay as described in Methods. Results are shown as mean of triplicate experiments. This is one of the representative results of 3 independent experiments.
Figure 8:
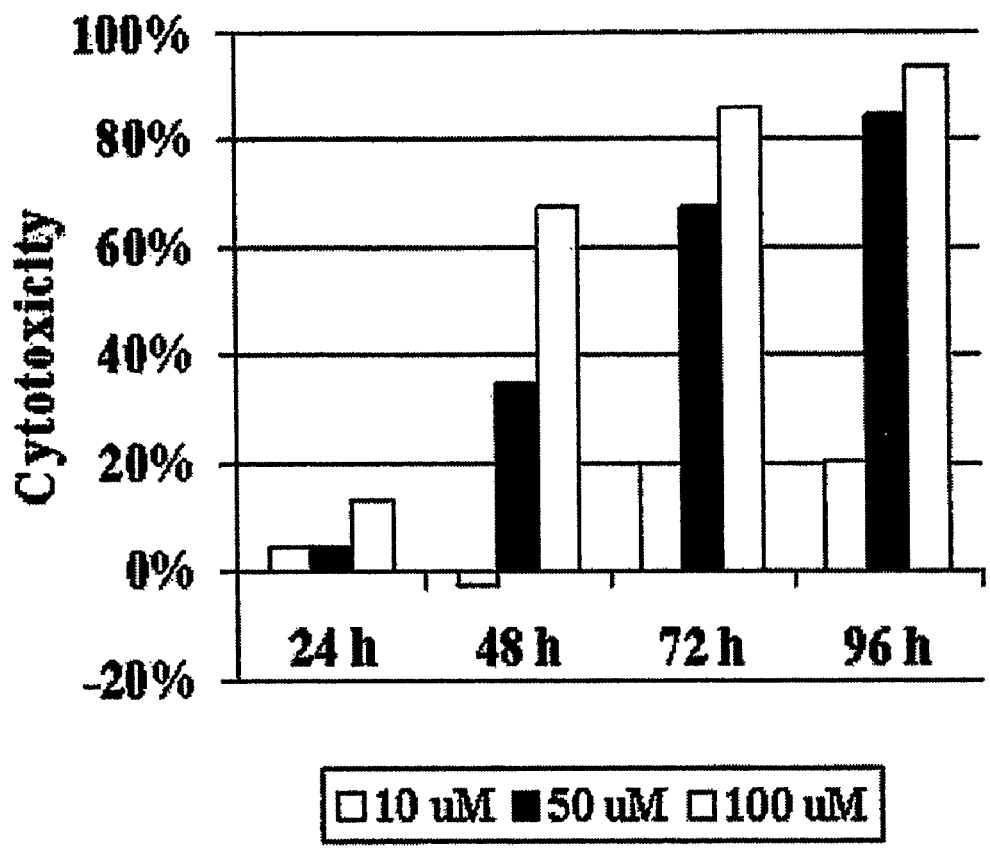
FIG. 8: Cytotoxicity dose-dependant of CLnA™ on MDA-MB-231 cells. Cells were exposed to different concentration of CLnA™ for different periods of time. Cytotoxicity was determined by colorimetric MTT cell proliferation assay as described in Methods. Results are shown as mean of triplicate experiments. This is one of the representative results of 3 independent experiments.

CLA and CLnA™ were shown to inhibit the proliferation of breast cancer cell lines in a dose-dependent manner. As can be seen from the results in FIGS. 7 and 8, maximum inhibition of cell proliferation occurred at 100 µM CLA or CLnA™. The same results were also observed on MCF-7 cells. These results provide evidence that a compound according to the invention, CLnA™, effectively inhibits dose-dependently the proliferation of human breast cancer cells.

Apoptosis or Necrosis

Cells can died either from apoptosis or necrosis. The inventors determined which death mechanism is induced by CLA and CLnA™. For this purpose, the inventors used fluorescence markers of cell death: YO-PRO1 is a specific dye for apoptotic cells while PI is a specific dye for necrotic cells.

Figure 9:
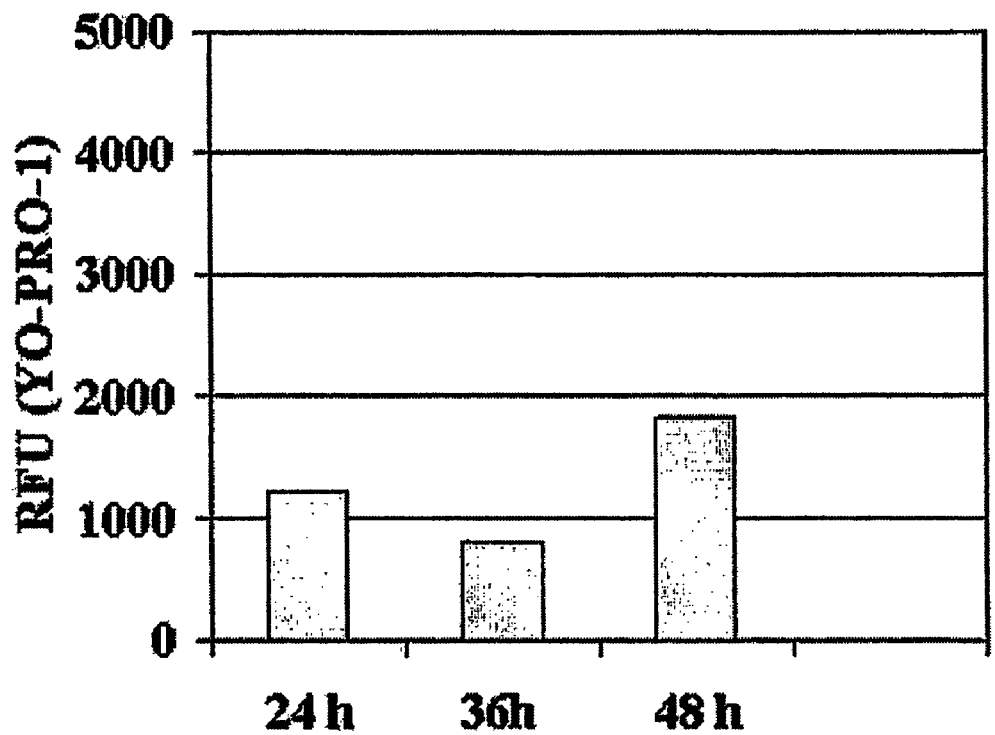
FIG. 9: Apoptosis induced by CLA (100 μM) on MDA-MB-231 cells. Cells were exposed to 100 μM CLA for different periods of time. Fluorescence of apoptotic cells was measured by YO-PRO-1 dye as described in Methods. Results are shown as mean of triplicate experiments. This is one of the representative results of 3 independent experiments.
Figure 10:
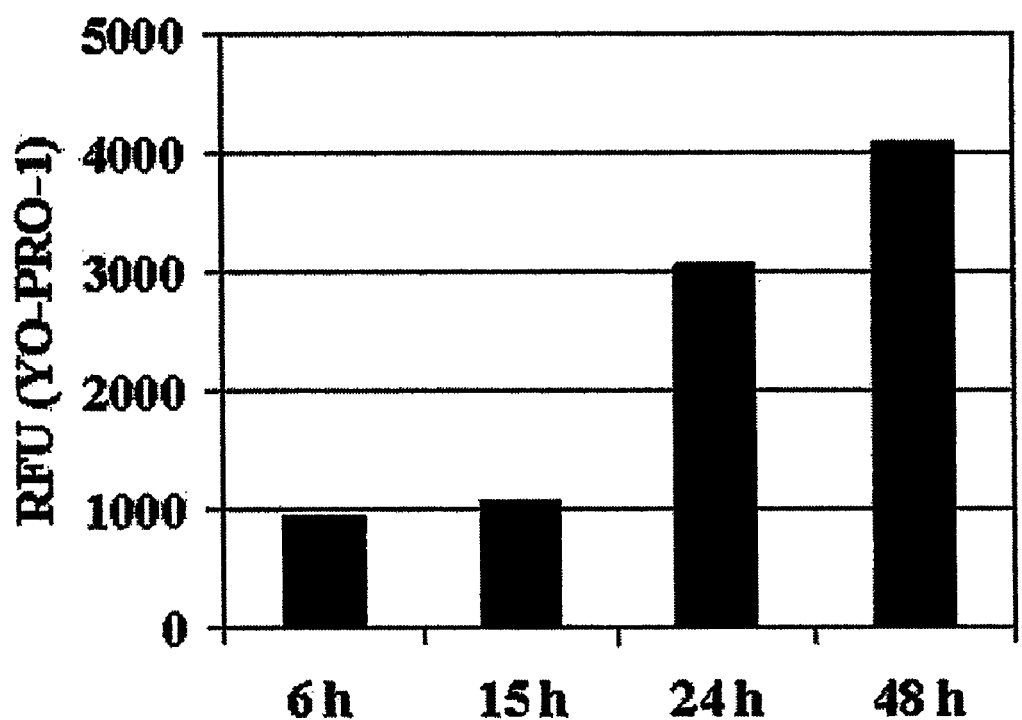
FIG. 10: Apoptosis induced by CLnA™ (100 μM) on MDA-MB-231 cells. Cells were exposed to 100 μM CLnA™ for different periods of time. Fluorescence of apoptotic cells was measured by YO-PRO-1 dye as described in Methods. Results are shown as mean of triplicate experiments. This is one of the representative results of 3 independent experiments.

When MDA-MB-231 cells were treated with CLA 100 µM for different period of time, there is a small increased in apoptosis (FIG. 9). When MDA-MB-231 cells are treated with CLnA™ 100 µM, there is a significant increase in the fluorescence of YO-PRO1 dye of apoptosis (FIG. 10). No necrosis was induced by CLnA™. The same results were also obtain in MCF-7 cells.

Fluorescence Microscopy

Apoptotic cells can be identified by PS exposure. Annexin V specifically bind to translocated PS. The hydrophilic dye PI has a high affinity for DNA but cannot pass the intact cell membrane (Nicolletti et al., 1991). PS exposure in the absence of PI is generally held as a characteristic for early apoptotic cells when only minor morphologic changes are detectable. In contrast, cells stained with both annexin V and PI have lost their membrane integrity and are considered to be late apoptotic or necrotic cells.

Using annexin V as a FITC conjugate in combination with PI as an exclusion dye for cell viability, this assay can detect apoptotic cells and discriminate between apoptosis and necrosis (Vermes et al, 1995). The annexin assay distinguished among early apoptosis, late apoptosis and apoptotic or necrotic phase in which the cells were labeled with both annexin V and PI. During early apoptosis, a loss of membrane asymmetry occurs when the PS is exposed on the outer leaflet of the plasma membrane. Annexin V will preferentially bind to PS and can therefore be used as an early indicator of apoptosis. In addition, PI can be used to assess plasma membrane integrity and cell viability. PI fluoresces red when bound to DNA or RNA, but is excluded from cells with intact plasma membranes.

Figure 11:
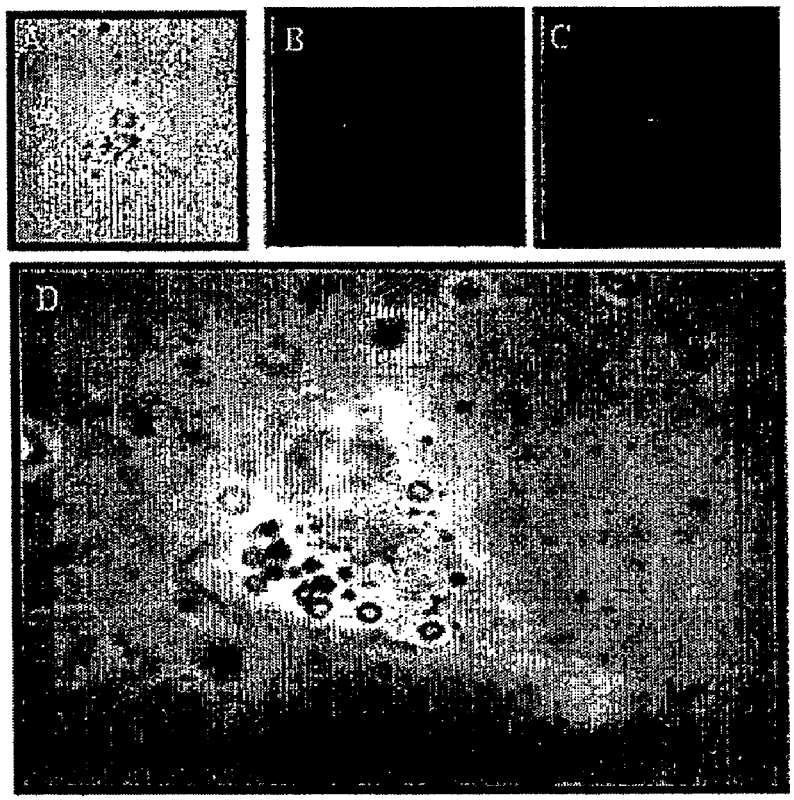
FIG. 11: Fluorescence microscopy of apoptosis induced by CLnA™ (100 μM) on MDA-MB-231 cells. Cells were exposed to 100 μM CLnA™ for 48 h. Fluorescence was measured using annexin V and PI dye as described in Methods. A: Photograph of MDA-MB-231 cells. Photographs were taken for annexin V (B) and PI (C). D is surempostion of the 3 photographs. Nuclei of apoptotic cell (green fluorescence) can be distinguished easily by PI red staining. This is one of the representative results of 3 independent experiments.

In FIG. 11, the green fluorescence represented the externalization of PS residues and was indicative of apoptotic cultures. The results of annexin V-FITC binding studies further substantiated the fact that CLnA™ induced cell death in human breast cancer cells is a result of an apoptotic cell death mechanism rather than a necrotic pathway. As the plasma membranes of cells become increasingly more permeable during the mid and late stage of apoptosis, PI becomes increasingly capable to penetrate the cells and staining nuclear DNA, producing a yellow red fluorescence signal.

In conclusion, CLnA™ is more cytotoxic than CLA on human breast cancer cell MDA-MB-231 and MCF-7. CLnA™ induce about 96% of cytotoxicity while CLA induce about 70% of cell death. CLnA™ is more apoptotic than CLA by at least 2 times. CLnA™ induced no necrosis. We also demonstrated that CLnA™ induced cell death by apoptosis with the use of annexin V and PI dyes. Both the MTT proliferation assay and the fluorescence assay showed that CLnA™ could inhibit cancer cells proliferation. The induction of apoptosis in human breast cancer cells suggest that CLnA™ could be used as a potential source of anti-cancer agents. Based on the foregoing results, it can be seen that CLnA™ has significant therapeutic application in the treatment or prevention of human cancers such as breast cancer, especially based on its inhibition of cancer cell proliferation and the induction of cancer cell apoptosis.

TABLE 1

FATTY ACIDS COMPOSITION FOR THE ISOMERIZED OIL AT DIFFERENT TIMES IN ASSAY #1

ISOMERISATION: Assay #1

| Fatty Acids | Linseed Oil | Propylene glycol | | Water | | | | | |
|---|---|---|---|---|---|---|---|---|---|
| | | | T = 160 C. | t = 1 h | T = 180 C. | t = 1.5 h | T = 180 C. | t = 2 h | |
| Saturated | | | | | | | | | |
| C16:0 | 5.40 | 5.53 | 5.25 | | 5.54 | | 5.56 | | |
| C18:0 | 4.13 | 4.26 | 4.09 | | 3.93 | | 4.28 | | |
| Total Saturated | | 9.79 | 9.34 | | 9.47 | | 9.84 | | |
| Monoenes | | | | | | | | | |
| C18:1 | 19.77 | 21.19 | 20.48 | | 20.68 | | 21.38 | | |
| Dienes | | | | | | | | | |
| C18:2 9c, 11t | 0.00 | 5.59 | 0.27 | | 1.17 | | 1.66 | | |
| C18:2 9c, 12c | 16.47 | 5.36 | 15.91 | | 14.37 | | 13.12 | | |
| C18:2 10t, 12c | 0.00 | 5.60 | 0.48 | | 1.46 | | 2.06 | | |
| Total C18:2 | 16.47 | 16.55 | 16.66 | | 17.00 | | 16.84 | | |
| Isomerisation C18:2 (conjugated/total) | 0.00 | 67.61% | 4.50% | | 15.47% | | 22.09% | | |
| Trienes | | | | | | | | | |
| C18:3 9c, 11t, 15c et C18:3 9c, 13t, 15c | 0.00 | 30.94 | 60.87% | 9.88 | 77.37% | 27.65 | 72.01% | 29.64 | 66.89% |
| C18:3 9c, 12c, 15c | 53.53 | 0.22 | | 39.94 | | 13.78 | | 6.86 | |
| C18:2 11, 13 cyclohexadiene | 0.00 | 8.32 | 16.37% | 0.61 | 4.78% | 5.44 | 14.17% | 7.40 | 16.70% |
| C18:3 conjugated | 0.00 | 11.57 | 22.76% | 2.28 | 17.85% | 5.31 | 13.83% | 7.27 | 16.41% |
| Total | 53.53 | 51.05 | | 52.71 | | 52.18 | | 51.17 | |
| Isomerisation C18:3 (conjugated/total) | 0.00 | 99.57% | 24.23% | | 73.59% | | 86.59% | | |
| Bilan (%) | 99.30 | 98.58 | 100% | 99.19 | 100% | 99.33 | 100% | 99.23 | 100% |

TABLE 2

FATTY ACIDS COMPOSITION FOR THE ISOMERIZED OIL AT DIFFERENT TIMES IN ASSAY #2

ISOMERISATION: Assay #2

| Fatty Acids | Linseed Oil | Propylene glycol | Water | | | | | |
|---|---|---|---|---|---|---|---|---|
| | | | T = 170 C. | t = 1 h | T = 170 C. | t = 2 h | T = 170 C. | t = 3 h |
| Saturated | | | | | | | | |
| C16:0 | 5.40 | 5.53 | 5.31 | | 5.17 | | 5.45 | |
| C18:0 | 4.13 | 4.26 | 4.17 | | 3.21 | | 4.18 | |
| Total Saturated | 9.53 | 9.79 | 9.48 | | 8.38 | | 9.63 | |
| Monoenes | | | | | | | | |
| C18:1 | 19.77 | 21.19 | 20.73 | | 18.43 | | 21.06 | |
| Dienes | | | | | | | | |
| C18:2 9c, 11t | 0.00 | 5.59 | 0.48 | | 0.89 | | 1.34 | |
| C18:2 9c, 12c | 16.47 | 5.36 | 15.50 | | 14.58 | | 13.82 | |

TABLE 2-continued

FATTY ACIDS COMPOSITION FOR THE ISOMERIZED OIL AT DIFFERENT TIMES IN ASSAY #2

ISOMERISATION: Assay #2

| Fatty Acids | Linseed Oil | Propylene glycol | | Water | | | | | |
|---|---|---|---|---|---|---|---|---|---|
| | | | | T = 170 C. | t = 1 h | T = 170 C. | t = 2 h | T = 170 C. | t = 3 h |
| C18:2 10t, 12c | 0.00 | 5.60 | | 0.71 | | 1.12 | | 1.68 | |
| Total C18:2 | 16.47 | 16.55 | | 16.69 | | 16.59 | | 16.84 | |
| Isomerisation C18:2 (conjugated/total) | 0.00 | 67.61% | | 7.13% | | 12.12% | | 17.93% | |
| Trienes | | | | | | | | | |
| C18:3 9c, 11t, 15c et C18:3 9c, 13t, 15c | 0.00 | 30.94 | 60.87% | 16.69 | 76.23% | 27.07 | 72.30% | 28.55 | 68.45% |
| C18:3 9c, 12c, 15c | 53.53 | 0.22 | | 30.45 | | 18.58 | | 10.00 | |
| C18:2 11, 13 cyclohexadiene | 0.00 | 8.32 | 16.37% | 1.79 | 8.18% | 4.94 | 13.19% | 6.47 | 15.51% |
| C18:3 conjugated | 0.00 | 11.57 | 22.76% | 3.41 | 15.59% | 5.43 | 14.50% | 6.69 | 16.04% |
| Total | 53.53 | 51.05 | | 52.34 | | 56.02 | | 51.71 | |
| Isomerisation C18:3 (conjugated/total) | 0.00 | 99.57% | | 41.83% | | 66.83% | | 80.66% | |
| Bilan (%) | 99.30 | 98.58 | 100% | 99.24 | 100% | 99.42 | 100% | 99.24 | 100% |

TABLE 3

FATTY ACIDS COMPOSITION FOR THE ISOMERIZED OIL AT DIFFERENT TIMES IN ASSAY #3

ISOMERISATION: Assay #3

| Fatty Acids | Linseed Oil | Propylene glycol | | Water | | | | | |
|---|---|---|---|---|---|---|---|---|---|
| | | | | T = 170 C. | t = 1 h | T = 170 C. | t = 2 h | T = 170 C. | t = 3 h |
| Saturated | | | | | | | | | |
| C16:0 | 5.40 | 5.53 | | 5.32 | | 5.45 | | 5.41 | |
| C18:0 | 4.13 | 4.26 | | 4.08 | | 4.2 | | 4.03 | |
| Total Saturated | 9.53 | 9.79 | | 9.40 | | 9.65 | | 9.44 | |
| Monoenes | | | | | | | | | |
| C18:1 | 19.77 | 21.19 | | 20.65 | | 21.13 | | 20.79 | |
| Dienes | | | | | | | | | |
| C18:2 9c, 11t | 0.00 | 5.59 | | 0.35 | | 0.68 | | 1.03 | |
| C18:2 9c, 12c | 16.47 | 5.36 | | 15.76 | | 15.25 | | 14.42 | |
| C18:2 10t, 12c | 0.00 | 5.60 | | 0.67 | | 1.04 | | 1.47 | |
| total C18:2 | 16.47 | 16.55 | | 16.78 | | 16.97 | | 16.92 | |
| isomerisation C18:2 (conjugated/total) | 0.00 | 67.61% | | 6.08% | | 10.14% | | 14.78% | |
| Trienes | | | | | | | | | |
| C18:3 9c, 11t, 15c et C18:3 9c, 13t, 15c | 0.00 | 30.94 | 60.87% | 12.92 | 75.73% | 19.44 | 71.93% | 24.26 | 68.69% |
| C18:3 9c, 12c, 15c | 53.53 | 0.22 | | 35.48 | | 24.79 | | 17.04 | |
| C18:2 11, 13 cyclohexadiene | 0.00 | 8.32 | 16.37% | 1.19 | 6.98% | 3.15 | 11.66% | 5.10 | 14.44% |
| C18:3 conjugated | 0.00 | 11.57 | 22.76% | 2.95 | 17.29% | 4.44 | 16.42% | 5.96 | 16.87% |
| Total | 53.53 | 51.05 | | 52.54 | | 51.82 | | 52.36 | |
| Isomerisation C18:3 (conjugated/total) | 0.00 | 99.57% | | 32.47% | | 52.16% | | 67.46% | |
| Bilan (%) | 99.30 | 98.58 | 100% | 99.37 | 100% | 99.57 | 100% | 99.51 | 100% |

TABLE 4

FATTY ACIDS COMPOSITION FOR THE ISOMERIZED OIL AT DIFFERENT TIMES IN ASSAY #4

ISOMERISATION: Assay #4

| Fatty Acids | Linseed Oil | Propylène glycol | Water 180 | t = 0.5 h | T = 180 C. | t = 1 h | T = 180 C. | t = 1.5 h | T = 180 C. | t = 2 h |
|---|---|---|---|---|---|---|---|---|---|---|
| Saturated | | | | | | | | | | |
| C16:0 | 5.40 | 5.53 | 5.4 | | 5.37 | | 5.43 | | 5.32 | |
| C18:0 | 4.13 | 4.26 | 4.1 | | 4.11 | | 4.21 | | 4.08 | |
| Total Saturated | 9.53 | 9.79 | 0.00 9.50 | | 9.48 | | 9.64 | | 9.40 | |
| Monoenes | | | | | | | | | | |
| C18:1 | 19.77 | 21.19 | 20.65 | | 20.92 | | 21.15 | | 20.99 | |
| Dienes | | | | | | | | | | |
| C18:2 9c, 11t | 0.00 | 5.59 | 0.94 | | 1.59 | | 2.50 | | 2.99 | |
| C18:2 9c, 12c | 16.47 | 5.36 | 14.39 | | 13.21 | | 11.23 | | 10.01 | |
| C18:2 10t, 12c | 0.00 | 5.60 | 1.31 | | 1.97 | | 2.98 | | 3.59 | |
| Total C18:2 | 16.47 | 16.55 | 16.64 | | 16.77 | | 16.71 | | 16.59 | |
| Isomerisation C18:2 (conjugated/total) | 0.00 | 67.61% | 13.52% | | 21.23% | | 32.79% | | 39.66% | |
| Trienes | | | | | | | | | | |
| C18:3 9c, 11t, 15c et C18:3 9c, 13t, 15c | 0.00 | 30.94 | 60.87% 25.36 | 72.96% | 29.91 | 67.36% | 31.49 | 63.59% | 31.24 | 61.46% |
| C18:3 9c, 12c, 15c | 53.53 | 0.22 | 18.07 | | 7.80 | | 2.10 | | 0.98 | |
| C18:2 11, 13 cyclohexadiene | 0.00 | 8.32 | 16.37% 4.54 | 13.06% | 7.35 | 16.55% | 9.02 | 18.21% | 9.60 | 18.89% |
| C18:3 conjugés | 0.00 | 11.57 | 22.76% 4.86 | 13.98% | 7.14 | 16.08% | 9.01 | 18.19% | 9.99 | 19.65% |
| Total | 53.53 | 51.05 | 52.83 | | 52.20 | | 51.62 | | 51.81 | |
| Isomérisation C18:3 (conjugated/total) | 0.00 | 99.57% | 65.80% | | 85.06% | | 95.93% | | 98.11% | |
| Bilan (%) | 99.30 | 98.58 | 100% 99.62 | 100% | 99.37 | 100% | 99.12 | 100% | 98.79 | 100% |

TABLE 5

FATTY ACIDS COMPOSITION FOR THE ISOMERIZED OIL AT DIFFERENT TIMES IN ASSAY #5

ISOMERISATION: Assay # 5

| Fatty Acids | Linseed Oil | Propylene glycol | Water 180 | t = 0.5 h | T = 180 C. | t = 1 h | T = 180 C. | t = 1.5 h | T = 180 C. | t = 2 h |
|---|---|---|---|---|---|---|---|---|---|---|
| Saturated | | | | | | | | | | |
| 16:0 | 5.40 | 5.53 | 5.32 | | 5.37 | | 5.27 | | 5.45 | |
| 18:0 | 4.13 | 4.26 | 4.09 | | 4.14 | | 4.15 | | 4.19 | |
| Total Saturated | 9.53 | 9.79 | 9.41 | | 9.51 | | 9.42 | | 9.64 | |
| Monoenes | | | | | | | | | | |
| 18:01 | 19.77 | 21.19 | 20.58 | | 20.83 | | 20.9 | | 21.15 | |
| Dienes | | | | | | | | | | |
| C18:2 9c, 11t | 0.00 | 5.59 | 0.40 | | 0.80 | | 1.26 | | 1.63 | |
| C18:2 9c, 12c | 16.47 | 5.36 | 15.59 | | 14.81 | | 13.77 | | 12.76 | |
| C18:2 10t, 12c | 0.00 | 5.60 | 0.68 | | 1.20 | | 1.81 | | 2.30 | |
| Total C18:2 | 16.47 | 16.55 | 16.67 | | 16.81 | | 16.84 | | 16.69 | |
| Isomerisation C18:2 (conjugated/total) | 0.00 | 67.61% | 6.48% | | 11.90% | | 18.23% | | 23.55% | |
| Trienes | | | | | | | | | | |
| C18:3 9c, 11t, 15c et C18:3 9c, 13t, 15c | 0.00 | 30.94 | 60.87% 11.79 | 77.11% | 18.71 | 69.58% | 23.75 | 65.21% | 26.65 | 62.54% |

TABLE 5-continued

FATTY ACIDS COMPOSITION FOR THE ISOMERIZED OIL AT DIFFERENT TIMES IN ASSAY #5

| | | | ISOMERISATION: Assay # 5 | | | | | | | |
|---|---|---|---|---|---|---|---|---|---|---|
| | | | Water | | | | | | | |
| Fatty Acids | Linseed Oil | Propylene glycol | | 180 | t = 0.5 h | T = 180 C. | t = 1 h | T = 180 C. | t = 1.5 h | T = 180 C. | t = 2 h |
| C18:3 9c, 12c, 15c | 53.53 | 0.22 | | 36.77 | | 25.23 | | 15.57 | | 9.05 | |
| C18:2 11, 13 cyclohexadiene | 0.00 | 8.32 | 16.37% | 0.58 | 3.79% | 3.25 | 12.09% | 5.34 | 14.66% | 6.78 | 15.91% |
| C18:3 conjugated | 0.00 | 11.57 | 22.76% | 2.92 | 19.10% | 4.93 | 18.33% | 7.33 | 20.13% | 9.18 | 21.54% |
| Total | 53.53 | 51.05 | | 52.06 | | 52.12 | | 51.99 | | 51.66 | |
| Isomérisation C18:3 (conjugated/total) | 0.00 | 99.57% | | 29.37% | | 51.59% | | 70.05% | | 82.48% | |
| Bilan (%) | 99.30 | 98.58 | 100% | 98.72 | 100% | 99.27 | 100% | 99.15 | 100% | 99.14 | 100% |

TABLE 6

FATTY ACIDS COMPOSITION FOR THE ISOMERIZED OIL AT DIFFERENT TIMES IN ASSAY #7

| | | | ISOMERISATION: Assay #7 | | | | | | | |
|---|---|---|---|---|---|---|---|---|---|---|
| | | | Water | | | | | | | |
| Fatty Acids | Linseed Oil | Propylene glycol | | 180 | t = 1 h | T = 180 C. | t = 2 h | T = 180 C. | t = 3 h | T = 180 C. | t = 4 h |
| Saturated | | | | | | | | | | | |
| 16:0 | 5.40 | 5.53 | | 5.29 | | 5.3 | | 5.38 | | 5.37 | |
| 18:0 | 4.13 | 4.26 | | 4.07 | | 4.13 | | 4.12 | | 4.11 | |
| Total Saturated | 9.53 | 9.79 | | 9.36 | | 9.43 | | 9.50 | | 9.48 | |
| Monoenes | | | | | | | | | | | |
| 18:01 | 19.77 | 21.19 | | 20.64 | | 20.78 | | 20.98 | | 20.13 | |
| Dienes | | | | | | | | | | | |
| C18:2 9c, 11t | 0.00 | 5.59 | | 0.51 | | 0.93 | | 1.36 | | 1.82 | |
| C18:2 9c, 12c | 16.47 | 5.36 | | 15.49 | | 14.38 | | 13.63 | | 12.68 | |
| C18:2 10t, 12c | 0.00 | 5.60 | | 0.78 | | 1.30 | | 1.82 | | 2.40 | |
| Total C18:2 | 16.47 | 16.55 | | 16.78 | | 16.61 | | 16.81 | | 16.90 | |
| Isomerisation C18:2 (conjugated/total) | 0.00 | 67.61% | | 7.69% | | 13.43% | | 18.92% | | 24.97% | |
| Trienes | | | | | | | | | | | |
| C18:3 9c, 11t, 15c et C18:3 9c, 13t, 15c | 0.00 | 30.94 | 60.87% | 14.87 | 75.91% | 22.61 | 68.58% | 26.51 | 67.52% | 28.19 | 63.51% |
| C18:3 9c, 12c, 15c | 53.53 | 0.22 | | 32.98 | | 19.55 | | 12.31 | | 7.62 | |
| C18:2 11, 13 cyclohexadiene | 0.00 | 8.32 | 16.37% | 1.79 | 9.14% | 4.17 | 12.65% | 5.98 | 15.23% | 6.94 | 15.63% |
| C18:3 conjugated | 0.00 | 11.57 | 22.76% | 2.93 | 14.96% | 6.19 | 18.77% | 6.77 | 17.24% | 9.26 | 20.86% |
| Total | 53.53 | 51.05 | | 52.57 | | 52.52 | | 51.57 | | 52.01 | |
| Isomerisation C18:3 (conjugated/total) | 0.00 | 99.57% | | 37.26% | | 62.78% | | 76.13% | | 85.35% | |
| Bilan (%) | 99.30 | 98.58 | 100% | 99.35 | 100% | 99.34 | 100% | 98.86 | 100% | 98.52 | 100% |

TABLE 7

FATTY ACIDS COMPOSITION FOR THE ISOMERIZED OIL IN ASSAY #8

ISOMERISATION: Assay #8

| Fatty Acids | Linseed Oil | Propylene glycol | Water T = 180 C. | t = 4 h |
|---|---|---|---|---|
| Saturated | | | | |
| 16:0 | 5.40 | 5.53 | 5.47 | |
| 18:0 | 4.13 | 4.26 | 4.11 | |
| Total Saturated | 9.53 | 9.79 | 9.58 | |
| Monoenes | | | | |
| 18:1 | 19.77 | 21.19 | 21.14 | |
| Dienes | | | | |
| C18:2 9c, 11t | 0.00 | 5.59 | 1.60 | |
| C18:2 9c, 12c | 16.47 | 5.36 | 13.23 | |
| C18:2 10t, 12c | 0.00 | 5.60 | 2.09 | |
| Total C18:2 | 16.47 | 16.55 | 16.92 | |
| Isomerisation C18:2 (conjugated/total) | 0.00 | 67.61% | 21.81% | |
| Trienes | | | | |
| C18:3 9c, 11t, 15c et C18:3 9c, 13t, 15c | 0.00 | 30.94 | 60.87% | 27.97 | 66.15% |
| C18:3 9c, 12c, 15c | 53.53 | 0.22 | | 9.43 | |
| C18:2 11, 13 cyclohexadiene | 0.00 | 8.32 | 16.37% | 6.47 | 15.30% |
| C18:3 conjugated | 0.00 | 11.57 | 22.76% | 7.84 | 18.54% |
| Total | 53.53 | 51.05 | | 51.71 | |
| Isomerisation C18:3 (conjugated/total) | 0.00 | 99.57% | | 81.76% | |
| Bilan (%) | 99.30 | 98.58 | 100% | 99.35 | 100% |

TABLE 8

FATTY ACIDS COMPOSITION FOR THE ISOMERIZED OIL IN ASSAY #9

ISOMERISATION: Assay # 9

| Fatty Acids | Linseed Oil Initial | Isomerisation (Propylene glycol) | Plukenetia volubilis Oil Initial | Isomerisation (Water) | |
|---|---|---|---|---|---|
| Saturated | | | | | |
| C16:0 | 5.40 | 5.53 | 3.74 | 4.19 | |
| C18:0 | 4.13 | 4.26 | 2.7 | 3.06 | |
| Total Saturated | 9.53 | 9.79 | 6.44 | 7.25 | |
| Monoenes | | | | | |
| C18:1 | 19.77 | 21.19 | 8.93 | 9.73 | |
| Dienes | | | | | |
| C18:2 9c, 11t | | 5.59 | | 11.61 | |
| C18:2 9c, 12c | 16.47 | 5.36 | 31.96 | 6.86 | |
| C18:2 10t, 12c | | 5.60 | | 12.43 | |
| Total C18:2 | 16.47 | 16.55 | | 30.90 | |
| Isomerisation C18:2 (conjugated/total) | | 67.61% | | 77.80% | |
| Trienes | | | | | |
| C18:3 9c, 11t, 15c C18:3 9c, 13t, 15c | | 30.94 | 60.87% | 30.08 | 60.08% |
| C18:3 9c, 12c, 15c | 53.53 | 0.22 | 51.82 | 0.38 | |
| C18:2 11, 13 cyclohexadiene | | 8.32 | 16.37% | 7.58 | 15.14% |
| C18:3 conjugated | | 11.57 | 22.76% | 12.41 | 24.79% |
| Total | 53.53 | 51.05 | | 50.45 | |
| Isomerisation C18:3 (conjugated/total) | | 99.57% | | 99.25% | |
| Bilan (%) | 99.30 | 98.58 | 100.00% | 105.59 98 | 100.00% |

TABLE 9

SUMMARY OF ISOMERIZATION CONDITIONS FOR DIFFERENT ASSAYS

| | | | | | | | | | | OUT* | | | |
|---|---|---|---|---|---|---|---|---|---|---|---|---|---|
| | | | IN | | | | | | | CLnA™ | CLA | | |
| | | Reagents | | | | | | | | C18:3 9c, | C18:2 9c, | Cyclic | |
| | | Propylene | | | | | Reaction Conditions | | | 11t, 15c | 11t | C18:2 11, 13 | |
| | Linseed Oil | | Glycol | | NaOH | | Total | Temperature | Sample Time | C18:3 9c, | C18:2 10t, | cyclo- | Satu- |
| Assay # | (g) | (%) | (g) | (%) | (g) | (%) | (g) | (° C.) | (h) | 13t, 15c | 12c | hexadiène | rated |
| 0 | 712 | 8.0% | 7,778 | 87.7% | 378 | 4.3% | 8,868 | 160.00 | 2.0 | 30.94 | 11.19 | 8.32 | 9.79 |

| | Linseed Oil | | Water | | NaOH | | Total | Temperature | Sample Time | | | | |
|---|---|---|---|---|---|---|---|---|---|---|---|---|---|
| Assay # | (g) | (%) | (g) | (%) | (g) | (%) | (g) | (° C.) | (h) | | | | |
| 1 | 712 | 8.0% | 7,778 | 87.7% | 378 | 4.3% | 8,868 | 180 | 1.0 1.5 2.0 | 29.64 | 3.72 | 7.40 | 9.84 |
| 2 | 1428 | 8.0% | 15,794 | 88.3% | 666 | 3.7% | 17,888 | 170 | 1.0 2.0 3.0 | 28.55 | 3.02 | 6.47 | 9.63 |
| 3 | 2804 | 14.2% | 15,556 | 79.0% | 1,324 | 6.7% | 19,684 | 170 | 1.0 2.0 3.0 | 24.26 | 2.05 | 5.10 | 9.44 |
| 4 | 1408 | 7.8% | 15,724 | 86.8% | 974 | 5.4% | 18,106 | 180 | 0.5 1.0 1.5 2.0 | 31.24 | 6.58 | 9.60 | 9.40 |
| 5 | 3520 | 23.0% | 10,904 | 71.3% | 866 | 5.7% | 15,290 | 180 | 0.5 1.0 1.5 2.0 | 26.65 | 3.93 | 6.78 | 9.64 |
| 7 | 2886 | 18.2% | 12264 | 77.4% | 686 | 4.3% | 15,836 | 180 | 1.0 2.0 3.0 4.0 | 28.19 | 4.22 | 6.94 | 9.48 |
| 8 | 2886 | 18.2% | 12292 | 77.5% | 686 | 4.3% | 15,864 | 180 | 4.0 | 27.97 | 3.69 | 6.47 | 9.58 |

| | *Plukenetia volubilis* Oil | | Water | | NaOH | | Total | Temperature | Sample Time | | | | |
|---|---|---|---|---|---|---|---|---|---|---|---|---|---|
| Assay # | (g) | (%) | (g) | (%) | (g) | (%) | (g) | (° C.) | (h) | | | | |
| 9 | 491 | 2.9% | 15508 | 90.1% | 1220 | 7.1% | 17,219 | 180 | 4 | 30.08 | 24.04 | 7.58 | 7.25 |

*Results corresponding to the last sample time.

TABLE 10

DIFFERENT PURIFICATION STEPS BY UREA CRYSTALLIZATION FOR CLnA ™ COMPOSITIONS

HOOC⌇⌇⌇⌇⌇⌇⌇⌇⌇

HOOC⌇⌇⌇⌇⌇⌇⌇⌇⌇

ᵃDifferent full conjugated C18:3 isomers
*Final product is combination of U4S and U5S

TABLE 11

COMPOSITION OF CLA AND DIFFERENT CLnA USED IN THE PRESENT INVENTION FOR CANCER TREATMENT

| | | | | CLA | CLnA | | | | |
|---|---|---|---|---|---|---|---|---|---|
| | Current Name | Configuration | #C | 100 | 40 | 50 | 58 | 75 | 90 |
| 1 | Palmitic | | 16:0 | | 0.90 | 0.37 | 0.51 | | 0.37 |
| 2 | Oleic | cis-9 | 18:1 | | 20.24 | 6.89 | 10.86 | 0.73 | 0.72 |
| 3 | Rumenic | cis-9, trans-11 | 18:2 | 52.00 | 6.46 | 5.36 | 7.05 | 2.16 | 0.64 |
| 4 | Linoleic | cis-9, cis-12 | 18:2 | | 7.16 | 6.81 | 8.90 | 11.89 | 0.44 |
| 5 | | trans-10, cis-12 | 18:2 | 48.00 | 6.74 | 6.80 | 8.77 | 3.79 | 0.71 |
| 6 | 11,13-cyclic CLA | | 18:2 | | 11.93 | 17.25 | 0.52 | 2.26 | 0.68 |
| 7 | Alpha Rumelenic Acid (α-CLNA) | cis-9, trans-11, cis-15 cis-9, trans-13, cis-15 | 18:3 | | 39.37 | 49.77 | 57.68 | 74.84 | 90.64 |
| 8 | Alpha Linolenic | cis-9, cls-12, cls-15 | 18:3 | | 0.41 | 0.37 | 0.38 | 1.21 | 1.88 |
| 9 | Conjugated Isomers | 10, 12, 14 | 18:3 | | 6.69 | 6.37 | 5.34 | 3.13 | 3.45 |

REFERENCES

Delany J P, West D B (2000) Changes in body composition with conjugated linoleic acid. *J Am Coil Nutr* 19(4):487S-493S.

Destaillats et al. (2003) Evidence for a conjugated linolenic acid (CLNA) in milk fat: cis-9, trans-11, cis-15. *Lipids* Sous presse.

Durgam, V R, Femandes G (1997) The growth inhibitory effect of conjugated linoleic acid on MCF-7 cells is related to estrogen response system. *Cancer Lett* 116:121-130.

Futakuchi m, Cheng J L, Hirose M, Kimoto N, Cho Y M, Iwata T, Kasai M, Tokudome S, Shirai R (2002) Inhibition of conjugated fatty acids derived from safflower or perilla oil of induction and development of mammary tumors in rats induced by 2-amino-1-methyl-6-phenylimidazol[4,5-b]pyridine (PhIP). *Cancer Lett* 178:131-139.

Ha Y L, Grimm N K, Pariza M W (1987) Anticarcinogens from fried ground beef: heat-altered derivatives of linoleic acid *Carcinogenesis* 8:1881-1887.

Harris W S, Park Y, Isley W I (2003) Cardiovascular disease and long-chain omega-3 fatty acids. *Curr Opin Lipidol* 14:9-14.

He K, Rimm E B, Merchant A, Rosner B A, Stampfer M J, Willett W C, Ascherio A (2002) Fish consumption and risk of stroke in men. *JAMA* 288(24):3130-3136.

Igarashi M, Miyazawa T (2000a) Doconjugated eicosapentaenoic acid and conjugated docosahexaenoic acid induce apoptosis via lipid peroxydation in cultured human tumors cells? *Biochem Biophys Res Commun* 270:649-656.

Igarashi M, Miyazawa T (2000b) Newly recognized cytotoxic effect of conjugated trienoic fatty acids on cultured human tumor cells. *Cancer Lett* 148:173-179.

Iso H, Rexrode K M, Stampfer M J, Manson J E, Colditz G A, Speizer F E, Hennekens C H, Willet W C (2001) Intake of fish and omega-3 fatty acids and risk of stoke in women. *JAMA* 285(3):304-312.

Ip C, Banni S, Angioni E, Carta G, McGinley J, Thompson H J, Barbano D, Bauman D (1999) Conjugated linoleic acid-enriched butter fat alters mammary gland morphogenesis and reduces cancer risk in rats. *J Nutr* 129(2):2135-2142.

Koba K, Akahoshi A, Yamasaki M, Tanaka K, Yamada K, Iwata T, Kamegai T, Tsutsumi K, Sugano M (2002) Dietary conjugated linolenic acid in relation to CLA differently modifies body fat mass and serum and liver lipid levels in rats. *Lipids* 37:343-350.

Krietchevsky D, Tepper S A, Wright S, TsoP, Czarnecki S K (2000) Influence of conjugated linoleic acid (CLA) on establishment and progression of atherosclerosis in rabbits. *J Am Coll Nutr* 19:472S-477S.

Lee K N, Kritchevsky D, Pariza M W (1994) Conjugated linoleic acid and atheroslerosis in rabbits *Atherosclerosis* 108:19-25.

Marchioli R, Schweiger C, Tavazzi L, Valagussa F (2001) Efficacyof n-3 polyinsaturated fatty acids after myocardial infarction: results of GISSI-prevenzione trial. Gruppo italiano per io studio della soprawivenza nell'infarto miocardico. *Lipids* 36:S119-S126.

Noone E J, Roche H M, Nugent A P, Gibney M J (2002) The effect of dietary supplementation using isomeric blends of conjugated linoleic acid on lipid metabolism in healthy human subjects. *Br J Nutr* 88(3):243-251.

Ostrowska E, Muralitharan M, Cross R F, Bauman D E, Dunshea F R (1999) Dietary conjugated linoleic acids increase lean tissue and decrease fat deposition in growing pigs. *J Nutr* 129:2037-2042.

Pariza M W, Ha Y L, Benjamin H, Sword J T, Gruter A, Chin S F, Storkson J, Faith N, Albright K. Formation and action of anticarcinogenic fatty acids. *Adv Exp Med Biol* 1991, 289:269-272.

Roche H M, Noone E, Sewter C, Mc Bennett S, Savage D, Gibney M J, O'Rahilly S, Vidal-Puig A J. Isomer-dependent metabolic effects of conjugated linoleic acid: insights from molecular markers sterol regulatory element-binding protein-1c and LXRalpha. *Diabetes* 51 (7):2037-44.

Ryder J W, Portocarrero C P, Song X M, Cui L, Yu M, Combatsiaris T, Galuska D, Bauman D E, Barbano D M, Charron M J, Zierath J R, Houseknecht K L (2001) Isomer-specific antidiabetic properties of conjugated linoleic acid. Improved glucose tolerance, skeletal muscle insulin action, and UCP-2 gene expression. *Diabetes* 50(5):1149-1157.

Skerrett P J, Hennekens C H (2003) Consumption of fish oils and decreased risk of stroke. *Prev Cardiol* Winter 6(1)38-41.

Thom E, Wadstein J, Gudmundsen O (2001) Conjugated linoleic acid reduces body fat in healthy exercising humans *J Int Med Res* 29(5):392-396.

West D B, Delany J P, Carnet P M, Blohm F, Truett A A, Scimeca J (1998) Effects od conjugated linoleic acid on body fat and energy metabolism in the mouse. *Am J Physiol* 275:R667-R672.

Fisher, P. B. (1984) in Tumor Promotion and Cocarcinogenesis *in Vitro*: Mechanisms of Tumor Promotion, ed. Slaga, T. J., (CRC, Boca Raton, Fla.), vol. 3, pp. 57-123.

Bishop, J. M. (1991). Cell 64, 235-248.

Knudson, A. G. (1991). Proc. Natl. Acad. Sci. USA 90, 10914-10921.

MacLachlan, T. K., Sang, N. & Giordano, A. (1995). Crit. Rev. Eukaryotic Gene Express. 5, 127-156.

Sang, N., Baldi, A. & Giordano, A. (1995). Mol. Cell. Differ. 3, 1-29.

Vermes I, Haanen C, Steffens-Nakken H, Reutelingsperger C. (1995) A novel assay for apoptosis. Flow cytometric detection of phosphatidylserine expression on early apoptotic cells using fluorescein labelled Annexin V. *J Immunol Methods* 184:39-51.

Winkler K, Steinhart H (2001) Identification of conjugated isomers of linolenic acid and arachidonic acid in cheese. *J Sep Sci* 24:663-668.

Y. L Ha, N K. Grimm and M. W. Pariza, in Carcinogenesis, Vol. 8, No. 12, pp. 1881-1887 (1987).

Y. L. Ha, N. K. Grimm and M. W. Pariza, in J. Agric. Food Chem., Vol. 37, No. 1, pp. 75-81 (1987).

The invention claimed is:

1. A process for the preparation of a composition comprising a mixture of linolenic acids, said linolenic acids being 9cis,11trans,15cis-octadecatrienoic acid and 9cis,13trans,15cis-octadecatrienoic acid, said process comprising the steps of:

providing a solvent of water;

blending with the solvent in the presence of a base one or a mixture of vegetable oils with various concentrations of linolenic acid or partial glycerides of such oils or partially purified and/or concentrated isomers to produce a reaction mixture; and recovering from the reaction mixture the composition comprising the mixture of linolenic acids, wherein the composition comprises a mixture of 9cis,13trans,15cis-octadecatrienoic acid and 9cis,11trans,15cis-octadecatrienoic acid in a ratio of 1:1 w/w, a concentration of said mixture varying between 30% and 90% by weight relative to the weight of the composition.

2. The process according to claim 1, wherein the step of blending is performed at a temperature ranging from 160° C. to 200° C.

3. The process according to claim 2, wherein the temperature is 180° C.

4. The process according to claim 1, wherein said process proceeds for a period varying between 0.5 hour to 4 hours.

5. The process according to claim 4, wherein the period is 2 hours.

6. The process of claim 1, wherein the vegetable oil comprises linseed oil, *Plukenetia volubilis* oil, borage oil or a mixture thereof.

7. The process of claim 1, wherein the base is selected from a group consisting of sodium hydroxide, sodium alkoxylate, sodium metal, potassium hydroxide, potassium alkoxylate and potassium metal.

8. The process according to claim 7, wherein the base is potassium hydroxide or sodium hydroxide.

9. A composition comprising a mixture of linolenic acids, said linolenic acids being 9cis,11trans,15cis-octadecatrienoic acid and 9cis,13trans,15cis-octadecatrienoic acid, wherein said linolenic acids are present in a ratio of 1:1 w:w and said mixture varying between 30% and 90% by weight relative to the weight of the composition, wherein the composition is prepared by
providing a solvent of water or polyol;
blending with the solvent in the presence of a strong base, one or a mixture of vegetable oil having various concentrations of linolenic acid or partial glycerides of such oils or partially purified and/or concentrated isomers, to produce a reaction mixture at a temperature of 160° C. to 200° C.; and
recovering from the reaction mixture the composition comprising the mixture of linolenic acids.

10. The composition according to claim 9, wherein it comprises at least 40% by weight of said mixture, and less than 0.5% by weight of 11,13-cyclic by-product.

11. A method for inducing apoptosis of mammalian solid neoplastic cancer cells, comprising contacting said cells with a therapeutically effective amount of the composition according to claim 9, wherein the mammalian solid neoplastic cancer cells are breast cancer cells.

12. The method of claim 11, wherein said breast cancer cells are human breast cancer cells.

13. The method of claim 12, wherein the human breast cancer cells are selected from the group consisting of estrogen positive and estrogen negative breast cancer cells.

14. The method of claim 13, wherein the breast cancer cells are from cells lines MB-231 or MCF-7.

15. The method of claim 14, wherein the step of contacting the cells with the composition is performed in vitro.

16. The process of claim 1, wherein before the step of blending, the base is mixed with the solvent of water.

17. The process of claim 8, wherein the base and the solvent of water are used in a relative proportion by weight between 4.2:100 and 8:100.

18. The process of claim 17, wherein the vegetable oil is linseed oil.

19. The process of claim 18, wherein the linseed oil is used in a relative proportion by weight to the base and solvent between 7.8:81.2 and 23:77.

20. The process of claim 18, further comprising, after producing the reaction mixture, the step of: cooling the reaction mixture to 60° C. and adding a stoichiometric amount of $CaCl_2$ to convert sodium soaps into calcium soaps.

21. The process of claim 20, further comprising, after producing the calcium soaps, the step of: filtering the mixture and washing with water.

22. The process of claim 21, further comprising, after filtering, the step of: adding a stoichiometric amount of $H_2SO_4$ in methanol to produce $CaSO_4$ precipitate at a pH of 3 to produce a free fatty acid solution.

23. The process of claim 22, further comprising, after producing the free fatty acid solution, the step of: subjecting the solution to repetitive urea crystallizations.

24. The process of claim 23, further comprising, after subjecting the composition to repetitive urea crystallizations, the step of: subjecting the composition to argentation liquid chromatography.

* * * * *